US008318661B2

(12) United States Patent
Ny et al.

(10) Patent No.: US 8,318,661 B2
(45) Date of Patent: Nov. 27, 2012

(54) CANDIDATES AGAINST INFECTION

(75) Inventors: Tor Ny, Umeå (SE); Jinan Li, Stockholm (SE); Yongzhi Guo, Umeå (SE)

(73) Assignee: Omnio Healer AB, Umeå (SE)

( * ) Notice: Subject to any disclaimer, the term of this patent is extended or adjusted under 35 U.S.C. 154(b) by 491 days.

(21) Appl. No.: 12/439,517

(22) PCT Filed: Aug. 28, 2007

(86) PCT No.: PCT/SE2007/050585
§ 371 (c)(1),
(2), (4) Date: Oct. 29, 2009

(87) PCT Pub. No.: WO2008/026999
PCT Pub. Date: Mar. 6, 2008

(65) Prior Publication Data
US 2010/0099600 A1   Apr. 22, 2010

Related U.S. Application Data

(60) Provisional application No. 60/823,665, filed on Aug. 28, 2006.

(51) Int. Cl.
*A61K 38/36* (2006.01)
(52) U.S. Cl. ....... 514/2.7; 514/13.6; 514/16.7; 514/21.2
(58) Field of Classification Search .................. None
See application file for complete search history.

(56) References Cited

U.S. PATENT DOCUMENTS

| | | | | |
|---|---|---|---|---|
| 6,054,122 A | * | 4/2000 | MacPhee et al. ............ | 424/94.4 |
| 2003/0026794 A1 | | 2/2003 | Fein | |

FOREIGN PATENT DOCUMENTS

| | | |
|---|---|---|
| CN | 1420126 A | 5/2003 |
| CN | 1768138 A | 5/2006 |
| EP | 0480906 A2 | 4/1992 |
| WO | WO-03/020297 A2 | 3/2003 |
| WO | WO-03/045466 A2 | 6/2003 |
| WO | WO-03/066842 A2 | 8/2003 |

OTHER PUBLICATIONS

Aderem, A. (2003). "Phagocytosis and the Inflammatory Response," *The Journal of Infectious Diseases* 187(Suppl 2):S340-345.
Alexander, C. M. et al. (1991). "Extracellular Matrix Degradation" Chapter 8 In *Cell Biology of Extracelluar Matrix*. E. D. Hay ed., 2nd Edition, Plenum Press: New York, pp. 255-302.
Carmeliet, P. et al. (Mar. 31, 1994). "Physiological Consequences of Loss of Plasminogen Activator Gene Function in Mice," *Nature* 368:419-424.
Chertov, O. et al. (2000). "Leukocyte Granule Proteins Mobilize Innate Host Defenses and Adaptive Immune Responses," *Immunological Reviews* 177:68-78.
Collen, D. et al. (Dec. 15, 1991). "Basic and Clinical Aspects of Fibrinolysis and Thrombolysis," *Blood* 78(12):3114-3124.
Cowan, S. T. et al. (1961). "Diagnostic Tables for the Common Medical Bacteria," *The Journal of Hygiene* 59:357-372.
Eriksson, P. O. et al. (2003). "First Forty-Eight Hours of Developing Otitis Media: An Experimental Study," *The Annals of Otology, Rhinology, and Laryngology* 112:558-566.
Eriksson, P. O. et al. (2006). "Spontaneous Development of Otitis Media in Plasminogen-Deficient Mice," *International Journal of Medical Microbiology* 296:501-509.
Gjertsson, I. et al. (2002). "Interleukin-10 Ameliorates the Outcome of *Staphylococcus aureus* Arthritis by Promoting Bacterial Clearance," *Clinical and Experimental Immunology* 130:409-414.
Gouguen, J. D. et al. (2000). "Role of the Pleiotropic Effects of Plasminogen Deficiency in Infection Experiments with Plasminogen-Deficient Mice," *Methods* 21:179-183.
Hauschildt, S. et al. (1995). "Bacterial Stimulators of Macrophages," *International Review of Cytology* 161:263-331.
International Preliminary Report on Patentability completed Dec. 12, 2008, for PCT Application No. PCT/SE2007/050585 filed Aug. 28, 2007, 10 pages.
International Search Report mailed Mar. 19, 2008, for PCT Application No. PCT/SE2007/050585 filed Aug. 28, 2007, 10 pages.
International Written Opinion mailed Sep. 3, 2008, for PCT Application No. PCT/SE2007/050585 filed Aug. 28, 2007, 16 pages.
Jin, T. et al. (Aug. 1, 2005). "Urokinase-Type Plasminogen Activator, an Endogenous Antibiotic," *The Journal of Infectious Diseases* 192:429-437.
Koutsu, Y. et al. (Dec. 1999). "Administration of Fibrinolysin and an Antibiotic in Periodontal Pockets," *Journal of the Osaka Odontological Society* 62(4):201-211. (English abstract on p. 211).
Levi, M. et al. (2005). "Two-Way Interactions Between Inflammation and Coagulation," *Trends in Cardiovascular Medicine* 15(7):254-259.
Li, J. (Feb. 2005). "Multifunctional Roles of Plasmin in Inflammation: Studies of Animal Models on Rheumatoid Arthritis, Multiple Sclerosis, Wound Healing and Infection," Doctoral Thesis, Department of Medical Biochemistry and Biophysics, Umea University, Sweden, p. 51.
Liu, Z.-Q. et al. (2001). "Staphylococcal Peptidoglycans Induce Arthritis," *Arthritis Research* 3(6):375-380.
Ny, A. et al. (1999). "Ovulation in Plasminogen-Deficient Mice," *Endocrinology* 140(11):5030-5035.
Ploplis, V. A. et al. (1995). "Effects of Disruption of the Plasminogen Gene on Thrombosis, Growth, and Health in Mice," *Circulation* 92:2585-2593.
Qasimi, P. et al. (Mar. 10, 2006). "Divergent Mechanisms Utilized by SOCS3 to Mediate Interleukin-10 Inhibition of Tumor Necrosis Factor α and Nitric Oxide Production by Macrophages," *The Journal of Biological Chemistry* 281(10):6316-6324.
Raaphorst. J. et al. (2001). "Early Inhibition of Activated Fibrinolysis Predicts Microbial Infection, Shock and Mortality in Febrile Medical Patients," *Thrombosis and Haemostatis* 86:543-549.
Saksela, O. et al. (1988). "Cell-Associated Plasminogen Activation: Regulation and Physiological Functions," *Annual Review of Cell Biology* 4:93-126.

(Continued)

*Primary Examiner* — Christina Bradley
(74) *Attorney, Agent, or Firm* — Morrison & Foerster LLP

(57) ABSTRACT

The present invention relates to the use of plasminogen/plasmin and its derivatives as agents for enhancing host defense against infection or other infectious diseases. The invention also relates to a method for screening of compounds which enhance host defense against infection by evaluating the host defense against bacterial arthritis and spontaneous otitis media in an animal model.

17 Claims, 19 Drawing Sheets

OTHER PUBLICATIONS

Smith, R. L. et al. (1997). "Staphylococcal Septic Arthritis: Antibiotic and Nonsteroidal Anti-Inflammatory Drug Treatment in a Rabbit Model," *Journal of Orthropaedic Research* 15:919-926.

Spier, I. R. et al. (1954). "Local Ambulatory Treatment of Chronic Leg Ulcers with Hyaluronidase, Plasminogen, and Antibiotics," *Surgery, Gynecology & Obstetrics* 98:667-674.

Teele, D. W. et al. (Jul. 1989). "Epidemiology of Otitis Media During the First Seven Years of Life in Children in Greater Boston: A Prospective, Cohort Study," *The Journal of Infection Diseases* 160(1):83-94.

Tefs, K. et al. (Nov. 1, 2006). "Molecular and Clinical Spectrum of Type I Plasminogen Deficiency: A Series of 50 Patients," *Blood* 108(9):3021-3026.

Travis, J. et al. (1983). "Control of Coagulation and Fibrinolysis by Plasma Proteinase Inhibitors," *Behring Institute of Mitteilungen* 73:56-65.

Wiman, B. et al. (1975). "Structural Relationship Between "Glutamic Acid" and "Lysine" Activation Peptide as Studied by Affinity Chromatography," *European Journal of Biochemistry* 50:489-494.

"Merk Manual Home Health Handbook Online", Periodontal Diseases, retrieved online on Feb. 24, 2012, 6 pages, online available at <http://www.merckmanuals.com/home/print/mouth_and_dental_disorders/periodontal_diseases/gingivitis.html>.

University of Maryland Medical Center Website, "Periodontal disease—Causes", retrieved online on Feb. 24, 2012, 4 pages, online available at <http://www.umm.edu/patiented/articles/what_causes_periodontal_disease_000024_3.htm>.

Office Action received for Australian Patent Application No. 2007290881, mailed on Feb. 21, 2012, 3 pages.

Office Action received for Australian Patent Application No. 2007290882, mailed on Feb. 8, 2012, 2 pages.

Office Action received for Chinese Patent Application No. 200780032092, issued on May 31, 2011, 17 pages (11 pages of English Translation and 6 pages of Office Action).

Office Action received for Chinese Patent Application No. 200780032405.1, issued on Jul. 27, 2011, 11 pages (7 pages of English Translation and 4 pages of Office Action).

Office Action received for Chinese Patent Application No. 200780032405.1, issued on Mar. 27, 2012, 11 pages (7 pages of English Translation and 4 pages of Office Action).

Extended European Search Report received for European Patent Application No. 07794195.3, mailed on Dec. 28, 2011, 7 pages.

Extended European Search Report received for European Patent Application No. 07794196.1, mailed on Dec. 28, 2011, 7 pages.

Office Action received for Eurasian Patent Application No. 200970233/13, mailed on Oct. 29, 2010, 4 pages (2 pages of English Translation and 2 pages of Office Action).

Notification of Readiness to Grant the Eurasian Patent received for Eurasian Patent Application No. 200970233/13, mailed on Mar. 28, 2011, 3 pages (2 pages of English Translation and 1 page of Notification).

Non Final Office Action Received for U.S. Appl. No. 12/439,516, mailed on Mar. 7, 2012, 12 pages.

Restriction Requirement received for U.S. Appl. No. 12/439,516, mailed on Nov. 14, 2011, 7 pages.

Alexander et al., "Proteinases and Extracellular Matrix Remodeling", Current Opinion in Cell Biology, vol. 1, 1989, pp. 974-982.

Andreasen et al., "The Urokinase-Type Plasminogen Activator System in Cancer Metastasis: A Review", International Journal of Cancer, vol. 72, 1997, pp. 1-22.

Berge et al., "PAM, a Novel Plasminogen-Binding Protein from Streptococcus Pyogenes", The Journal of Biological Chemistry, vol. 268, No. 34, Dec. 5, 1993, pp. 25417-25424.

Brandtzaeg et al., "Plasminogen Activator Inhibitor 1 and 2, Alpha-2-Antiplasmin, Plasminogen and Endotoxin Levels in Systemic Meningococcal Disease", Thrombosis Research, vol. 57, 1990, pp. 271-278.

Broder et al., "Isolation of a Prokaryotic Plasmin Receptor. Relationship to a Plasminogen Activator Produced by the Same Micro-Organism", The Journal of Biological Chemistry, vol. 266, No. 8, Mar. 15, 1991, pp. 4922-4928.

Clark et al., "Mechanisms of Initiation and Progression of Periodontal Disease", Periodontology 2000, vol. 2, 1993, pp. 72-82.

Collen, D., "Ham-Wasserman Lecture: Role of the Plasminogen System in Fibrin-Homeostasis and Tissue Remodeling", Hematology, 2001, pp. 1-9.

Fuchs et al., "*Borrelia burgdorferi* Induces Secretion of Pro-Urokinase-Type Plasminogen Activator by Human Monocytes", Infection and Immunity, vol. 64, No. 10, Oct. 1996, pp. 4307-4312.

Guo et al., "Beneficial and Detrimental Effects of Plasmin(ogen) during Infection and Sepsis in Mice", PLoS ONE, vol. 6, No. 9, Sep. 2011, p. e24774.

Guo et al., "Protective Effects of Plasmin(ogen) in a Mouse Model of *Staphylococcus aureus*—Induced Arthritis", Arthritis & Rheumatism, vol. 58, No. 3, Mar. 2008, pp. 764-772.

Harrington, D J., "Bacterial Collagenases and Collagen-Degrading Enzymes and Their Potential Role in Human Disease", Infection and Immunity, vol. 64, No. 6, Jun. 1996, pp. 1885-1891.

He et al., "Tissue Cooperation in a Proteolytic Cascade Activating Human Interstitial Collagenase", Proceedings of the National Academy of Sciences of the United States of America, vol. 86, Apr. 1989, pp. 2632-2636.

Kimura et al., "Induction of Experimental Periodontitis in Mice with *Porphyromonas gingivalis*-Adhered Ligatures", Journal of Periodontology, vol. 71, No. 7, Jul. 2000, pp. 1167-1173.

Klemm et al., "Fimbriae-Assisted Bacterial Surface Display of Heterologous Peptides", International Journal of Medical Microbiology, vol. 290, 2000, pp. 215-221.

Lahteenmaki et al., "Bacterial Plasminogen Activators and Receptors", FEMS Microbiology Reviews, vol. 25, 2001, pp. 531-552.

Lahteenmaki et al., "Immobilization of Plasminogen on *Escherichia coli* Flagella", FEMS Microbiology Letters, vol. 106, 1993, pp. 309-314.

Liakoni et al., "Bacterial Penetration of Pocket Soft Tissues in Chronic Adult and Juvenile Periodontitis Cases. An Ultrastructural Study", Journal of Clinical Periodontology, vol. 14, 1987, pp. 22-28.

Mignatti et al., "Biology and Biochemistry of Proteinases in Tumor Invasion", Physiological Reviews, vol. 73, No. 1, Jan. 1993, pp. 161-195.

Pancholi et al., "α-Enolase, a Novel Strong Plasmin(ogen) Binding Protein on the Surface of Pathogenic *Streptococci*", The Journal of Biological Chemistry, vol. 273, No. 23, Jun. 5, 1998, pp. 14503-14515.

Paul et al., "Matrix Metalloproteinases Contribute to the Blood-Brain Barrier Disruption During Bacterial Meningitis", Annal of Neurology, vol. 44, 1998, pp. 592-600.

International Preliminary Report on Patentability received for PCT Patent Application No. PCT/SE2007/050586, mailed on Dec. 12, 2008, 10 pages.

International Search Report received for PCT Patent Application No. PCT/SE2007/050586, mailed on Mar. 19, 2008, 9 pages.

International Written Opinion received for PCT Patent Application No. PCT/SE2007/050586, mailed on Mar. 19, 2008, 16 pages.

Rams et al., "*Staphylococci* in Human Periodontal Diseases", Oral Microbiology and Immunology, vol. 5, 1990, pp. 29-32.

Raum et al., "Synthesis of Human Plasminogen by the Liver", Science, vol. 208, May 30, 1980, pp. 1036-1037.

Rifkin et al., "Growth Factor Control of Extracellular Proteolysis", Cell Differentiation and Development, vol. 32, 1990, pp. 313-318.

Rifkin et al., "Proteolytic Control of Growth Factor Availability", APMIS, vol. 107, 1999, pp. 80-85.

Schott et al., "Therapy with a Purified Plasminogen Concentrate in an Infant with Ligneous Conjunctivitis and Homozygous Plasminogen Deficiency", The New England Journal of Medicine, vol. 339, No. 23, Dec. 3, 1998, pp. 1679-1686.

Scully et al., "Oral Lesions Indicative of Plasminogen Deficiency (Hypoplasminogenemia)", Oral Surgery, Oral Medicine, Oral Pathology, Oral Radiology and Endodontics, vol. 91, No. 3, Mar. 2001, pp. 334-337.

Sottrup-Jensen et al., "Amino-Acid Sequence of Activation Cleavage Site in Plasminogen: Homology with "Pro" Part of Prothrombin", Proceedings of the National Academy of Sciences of the United States of America, vol. 72, No. 7, Jul. 1975, pp. 2577-2581.

Sulniute et al., "Plasmin is Essential in Preventing Periodontitis in Mice", The American Journal of Pathology, vol. 179, No. 2, Aug. 2011, pp. 819-828.

Wallen, P, "Biochemistry of Plasminogen", in Fibrinolysis, D. L. Kline et al. eds, CRC Press: Baca Raton, Florida, 1980, pp. 2-25.

Werb et al., "Endogenous Activation of Latent Collagenase by Rheumatoid Synovial Cells. Evidence for a Role of Plasminogen Activator", The New England Journal of Medicine, vol. 296, No. 18, May 5, 1977, pp. 1017-1023.

* cited by examiner

CANDIDATES AGAINST INFECTION

CROSS REFERENCE TO RELATED APPLICATIONS

This application is a U.S. National Phase patent application of PCT/SE2007/050585, filed Aug. 28, 2007, which claims priority to U.S. Provisional Application Ser. No. 60/823,665, filed Aug. 26, 2006, the contents of which are hereby incorporated by reference in the present disclosure in their entirety.

FIELD OF INVENTION

This invention relates to compounds and methods for prophylaxis, prevention, and/or treatment of infectious diseases and necrotic conditions affecting the extracellular matrix, especially due to bacteria. In particular, the invention relates to such compounds and methods which result in improved infection defense, better cleaning of necrotic tissue as well as creating a functional and aesthetically satisfactory tissue remodeling. The invention also relates to animal models for studying bacterial infection and tissue necrosis, and screening methods for identifying and evaluating drugs and for enhancing treatment methods against bacterial infection and tissue necrosis.

BACKGROUND

Infectious diseases are caused by pathogens such as bacteria and viruses and eukaryotic organisms ranging from single-celled fungi and protozoa, through large complex metazoan such as parasitic worms. Pathogenic bacteria may contain virulence factors that mediate interactions with the host, eliciting particular responses from the host cells that promote the replication and spread of the pathogen. Viruses rely on subverting the machinery of the host cell to produce their proteins and to replicate their genomes. Pathogens often colonize the host by adhering to or invading the epithelial surfaces that are in direct contact with the environment. Viruses rely largely on receptor-mediated endocytosis for host cell entry, while bacteria exploit cell adhesion and phagocytic pathways (1). Pathogenic fungi, protozoa and other eukaryotic parasites typically pass through several different forms during the course of infection; the ability to switch among these forms is usually required for the parasites to be able to survive in a host and cause disease.

During the initial hours and days of host exposure to a new pathogen, the innate immune system is the first line of defense against invading pathogens. However, the initiation of specific adaptive immune responses is also required. Innate immune responses rely on the body's ability to recognize conserved features of pathogens that are not present in the uninfected host. These include many types of molecules on microbial surfaces and the double-stranded RNA of some viruses. Surface molecules of microorganisms also activate the complement system to target these organisms for phagocytosis by macrophages and neutrophils, and to produce an inflammatory response.

Bacteria have developed different strategies to escape from phagocytes. For instance, they can inhibit chemotaxis and phagocytosis, kill or colonize the phagocytes. The phagocytic cells use a combination of degrading enzymes, anti-microbial peptides and reactive oxygen species to kill the invading microorganisms (2). In addition, they release signaling molecules that trigger an inflammatory response and begin to marshal the forces of the adaptive immune system. Bacteria, on the other hand, have developed different strategies directed against the adaptive immune system such as molecular mimicry, suppression of antibodies, hiding inside cells, or release of antigen into the bloodstream (3).

Intracellular pathogens, including all viruses and many bacteria and protozoa, replicate inside a host cell, which they invade by one of a variety of mechanisms. Viruses rely largely on receptor-mediated endocytosis for host cell entry, while bacteria exploit cell adhesion and phagocytic pathways. Protozoa employ unique invasion strategies that usually require significant metabolic expense. Once inside, intracellular pathogens seek out a niche that is favorable for their replication, frequently altering host cell membrane traffic and exploiting the cytoskeleton for intracellular movement.

*Staphylococcus aureus* is a microorganism frequently associated with bacterial arthritis, which results in synovial inflammation, cartilage and bone destruction, and eventually joint deformity. Various animal species including mammals, birds and reptiles have been observed to develop spontaneous *S. aureus* arthritis and are therefore potential models for the induction of the disease.

The plasminogen activator (PA) system is a general proteolytic system that has been suggested to play an important role in the development of different types of arthritis. Plasminogen can be activated to the broad-spectrum protease plasmin by either of the two physiological PAs, tissue-type PA (tPA) or urokinase-type PA (uPA).

Otitis media is defined as inflammatory conditions of the ear. Otitis media is the most common childhood disease except for the common cold. The most important etiological factor related to otitis media is bacterial or viral infections of the upper respiratory tract. Otitis media is generally benign and a self-limiting disease, but despite this, the prescription rate of antibiotics is high. In fact, effects of antibiotics in curing otitis media lack evidence and so far surgical intervention is the therapy of choice for the treatment of recurrent acute otitis media (AOM) and chronic otitis media or otitis media with effusion (OME).

It is well known that the immediate colonization by the patient's normal skin flora (i.e. *S. aureus* and *Streptococcus pyogenes*) occurs following injury. Especially after the introduction of penicillin G in the early 1950s, which resulted in the virtual elimination of *Streptococcus pyogenes* as a cause of infection in thermally injured patients, *S. aureus* became the principal etiological agent of wound infection. Therefore *S. aureus* is one of the most common bacterium species on open-wound infection. Incisional wounds and burn wounds are the most common wound types observed in clinical practice.

Antibiotics and other antimicrobial drugs have been widely used in treatment of infectious diseases since the World War II era. The success of antimicrobials against disease-causing microbes is among modern medicine's great achievements. However, many antimicrobials are not as effective as they used to be due to the development of drug resistance. A key factor in the development of antibiotic resistance is the ability of infectious organisms to adapt quickly to new environmental conditions. Over time, some bacteria have developed ways to circumvent the effects of antibiotics. Widespread use of antibiotics is thought to have spurred evolutionarily adaptations that enable bacteria to survive these powerful drugs. Antimicrobial resistance provides a survival benefit to microbes and makes it harder to eliminate infections from the body. Ultimately, the increasing difficulty in fighting off microbes leads to an increased risk of acquiring infections in a hospital or other setting. Diseases such as tuberculosis, gonorrhea, malaria, and childhood ear infections are now more difficult to treat than they were just a few years ago. Drug resistance is an especially difficult problem for hospitals harboring critically ill patients who are less able to fight off infections without the help of antibiotics. Heavy use of antibiotics in these patients selects for changes in bacteria that bring about drug resistance. Unfortunately, this worsens the problem by producing bacteria with a greater ability to survive even in the presence of the strongest antibiotics. These even stronger drug-resistant bacteria continue to prey on vulnerable hospital patients. Therefore, there is an increasing awareness that novel therapeutical strategies are highly needed to improve the infection defense against infection.

Necrosis is the name given to unprogrammed or accidental death of cells and living tissue. It is less orderly than apoptosis, which are part of programmed cell death. In contrast to apoptosis, cleanup of cell debris resulting from necrosis by phagocytes of the immune system is generally more difficult, as the disorderly death generally does not send "eat-me" cell signals which tell nearby phagocytes to engulf the dying cell. This lack of signaling makes it harder for the immune system to locate and recycle dead cells which have died through necrosis than if the cell had undergone apoptosis. The release of intracellular content after cellular membrane damage is the cause of inflammation in necrosis.

There are many causes of necrosis including injury, infection, cancer, infarction, invenomation and inflammation. Severe damage to one essential system in the cell leads to secondary damage to other systems, a so-called "cascade of effects". Necrosis is caused by special enzymes that are released by lysosomes which are capable of digesting cell components or the entire cell itself. The injuries received by the cell may compromise the lysosome membrane, or may set off an unorganized chain reaction which causes the release in enzymes. Unlike in apoptosis, cells that die by necrosis may release harmful chemicals that damage other cells. Biopsy material necrosis is halted by fixation or freezing.

Currently there are four major therapeutical methods to cure necrosis. The first is surgical removal, which is the most rapid, and therefore is recommended when large necrotic areas or thick eschar present. The second is mechanical removal, which includes hydrotherapy, dextranomers and wound irrigation. The third is enzymatic removal 1, the enzyme used is mainly collagenase (eg: Santyl), however, the effect is too slow when infection presents; and fourthly is through autolytic method, which is via enzymes in wound fluid but the effect is extremely slow. However, none of the four treatment methods provide a functional and aesthetically satisfactory necrosis removal and tissue remodeling. Therefore, a novel therapeutic strategy is in great need in order to achieve a successful removal of necrosis.

Current therapeutic methods for treating infections such as bacterial arthritis, open wound infection, otitis media and necrosis have drawbacks as discussed above. Therefore, there is a great need in the art for improved strategies for treating infections in general.

SUMMARY OF THE INVENTION

The present invention relates to the surprising discovery that components of the plasminogen-activation pathway, and compounds with the capacity to activate plasminogen can be used for new and improved strategies for infectious diseases and tissue necrosis. An aspect of the invention relates to the ability of plasminogen, or other members of the plasminogen-activation pathway or compounds with the capacity to activate plasminogen, to play a role in protecting against e.g. *S. aureus*-induced arthritis and open wound infection by activating inflammatory cells, killing bacteria, removing necrotic tissue and enhancing cytokine expression. Such infection conditions further include infectious diseases and other diseases where tissue infection is commonly observed, for instance during tissue-specific infection defense, overall-body infection defense, acute infections, chronic infections, chronic ulcers, open wound infection and diabetic ulcers.

In certain embodiments, the invention relates to a method for the prophylaxis, prevention and/or treatment of infectious disease comprising administering an effective amount of a compound that is a component of the plasminogen-activating pathway or has the capacity to activate plasminogen directly or via the plasminogen-activating pathway.

In certain embodiments, the compounds with the capacity to activate plasminogen directly or via the plasminogen-activating pathway include streptokinase, saruplase, alteplase, reteplase, tenecteplase, anistreplase, monteplase, lanoteplase, pamiteplase, staphylokinase and recombinant forms and variants of the components of the plasminogen-activating pathway.

In certain embodiments, the infectious disease is a bacterial infectious disease or a viral infectious disease.

In additional embodiments, the bacterial infectious disease is selected from otitis media, bacterial arthritis, gingivitis, periodontitis, conjunctivitis, wound infection, surgical wound infections, necrosis, pneumonia, injuries in the respiratory organs caused by burns and/or infections and infected chronic leg ulcers in patients suffering from diabetes, venous or combined venous/arterial insufficiency or infectious arthritis or the like, injuries in the joint tissues caused by infections, preferably otitis media or bacterial arthritis.

In certain embodiments, the composition comprises a combination of two or more compounds. In certain embodiments, the composition further comprises at least one antibiotic agent.

In additional embodiments, the antibiotic agent is selected from the group consisting of tetracyclines, amphenicols, beta-lactams, penicillins, sulphonamides, macrolides, lincosamides, streptogamins, streptomycins, quinolones and metronidazoles.

In certain embodiments, the subject is mammal, and in particular a human. In additional embodiments the subject is deficient in plasmin or plasminogen. The deficiency can be congenital, acquired and/or local.

In certain embodiments, the compound is administered systemically, locally, topically, intravenously, intramuscularly, subcutaneously, via inhalation, intrathecally, via local injection, via intra-articular injection or rectally. In a preferred embodiment topical administration and/or local injection are used.

In certain embodiments, the compound is administered in combination with a suitable polypeptide carrier and/or one or more stabilizing agent In yet additional embodiments, the compound is administered at a dose of 0.0001 to about 1 g, preferably 0.005 mg to about 100 mg, more preferably from about 0.05 to about 50 mg. The dose in mg is in relation to square centimeter of infected area (i.e. mg/square centimeter infected area).

In further embodiments, the administration of the compound is repeated at least once, preferably at least every day.

In further embodiments, the administration is performed by applying a wound dressing, comprising the compound of the present invention, to an infected area.

In additional embodiments, the invention relates to a method for the prophylaxis, prevention and/or treatment of infectious disease, which comprises administering a pharmaceutical composition comprising an effective amount of a suitable compound to a subject in need of such treatment.

In certain embodiments, the invention relates to a pharmaceutical composition for the prophylaxis, prevention and/or treatment of infectious disease comprising an effective amount of a suitable compound.

In certain embodiments, the invention relates to a kit for use in the prophylaxis, prevention and/or treatment of infectious disease comprising an effective amount of a suitable compound and at least one antibiotic or antimycotic agent, in separate vials.

In certain embodiments, the invention relates to a method of identifying an agent that is useful in promoting host defense against infection, comprising the steps of: a) administering a test agent to an animal having a bacterial arthritis; b) evaluating at least one of the parameters: (i) the extent of killing bacteria, (ii) necrotic tissue formation, (iii) inflammatory cell activation, (iv) cytokine expression of the infection e.g. bacterial arthritis: c) comparing the chosen parameter(s) of step (b) with a control value; and d) selecting any test agent for which the chosen parameter(s) is(are) more beneficial compared to the control value as an agent useful in promoting host defense against infection.

In certain embodiments, the animal is selected from a member of the group consisting of a wild-type animal and a transgenic animal lacking endogenous expression of plasminogen.

In certain embodiments, the invention relates to a method for diagnosis of an ongoing infection, comprising determining the diagnostic presence of plasminogen.

In certain embodiments, the invention relates to a kit for use in the determination of plasminogen in a sample from a patient, wherein the sample is from body fluids, serum, excreted waste products, such as urine or faeces, exhalation air, or the like, in order to determine an ongoing infection and/or the effect of an ongoing treatment, comprising a plasminogen determinant and means for collecting, storing and/or examining the patient sample.

DESCRIPTION OF THE INVENTION

The present results in the ear showed that plasminogen plays a role in protecting against the spontaneous development of chronic otitis media. The present results also suggest using plasminogen for clinical therapy of certain types of otitis media. Therefore, these findings suggest that components of the plasminogen-activation pathway have a role in prevention and treatment of any infectious disease as a novel pro-inflammatory factor. In particular, the pro-inflammatory effects of components of the plasminogen-activation pathway include activating inflammatory cells, killing bacteria, removing necrotic tissue and enhancing cytokine expression and improving proper tissue remodeling. This conclusion is drawn based on the understanding of the overall host defense mechanism against all the infectious pathogens, the vast and versatile infectious diseases induced by $S.$ $aureus$, which is the major bacterium species used in our studies, and various infection models studied in this patent application (including infectious arthritis, burn induced infection, incision induced infection and otitis media).

Infectious diseases currently cause about a third of all human deaths in the world, more than all forms of cancer combined. Many types of pathogens cause disease in humans. The most familiar are viruses and bacteria. Other infectious pathogens are eukaryotic organisms, ranging from single-celled fungi and protozoa, through large complex metazoan such as parasitic worms. Each individual pathogen causes disease in different way, which makes it challenging to understand the basic biology of infection. However, all pathogens share the ability to interact with host cells in ways that promote replication and spread of the pathogen, but these host-pathogen interactions are diverse. Pathogens often colonize the host by adhering to or invading through the epithelial surfaces such as skin surface that is in direct contact with the environment. Intracellular pathogens, including all viruses and many bacteria and protozoa, replicate inside a host cell, which they invade by one of a variety of mechanisms. Viruses rely largely on receptor-mediated endocytosis for host cell entry, while bacteria exploit cell adhesion and phagocytic pathways. Protozoa employ unique invasion strategies that usually require significant metabolic expense. Once inside, intracellular pathogens seek out a niche that is favorable for their replication, frequently altering host cell membrane traffic and exploiting the cytoskeleton for intracellular movement. Besides altering the behavior of the individual host cells, pathogens frequently alter the behavior of the host organism in ways that favor spread to a new host. Pathogens evolve rapidly, so new infectious diseases frequently emerge, and old diseases acquire new ways to evade human attempts at treatment, prevention and eradication.

Furthermore, with the great progress against infectious diseases such as vaccines and antibiotics, pathogens have also developed drug resistance through 1) producing an enzyme that destroys the drug, 2) altering molecular target of the drug so that it is no longer sensitive the drug, or 3) preventing access to the target. Therefore, drug resistant pathogens are a growing problem.

Despite the various ways that pathogens have developed to invade human beings, there are only limited patterns that host defense machinery reacts against the infection. The host defense machinery includes both adaptive immune system and innate immune system. Whereas the adaptive immune system remembers previous encounters with specific pathogens and destroys them with the help of the innate immune system when they attack again, the innate immune system is not specific to a particular pathogen in the way that the adaptive immune system is. Thus, the innate immune system is the first line of defense against invading pathogens and it is also required to initiate specific adaptive immune responses.

Innate immune responses rely on the body's ability to recognize conserved features of pathogens that are not present in the uninfected host. These features include, for instance, peptidoglycan cell wall and flagella of bacteria, as well as lipopolysaccharide (LPS) on Gram-negative bacteria and teichoic acids on Gram-positive bacteria, zymosan, glucan and chitin in the cell walls of fungi and the double-stranded RNA of most viruses. Many of these pathogen-specific molecules are recognized by Toll-like receptor proteins on inflammatory cells. In vertebrates, microbial surface molecules also activate complement, a group of blood proteins that act together to disrupt the membrane of the microorganism, to target microorganisms for phagocytosis by macrophages and neutrophils, and to produce an inflammatory responses. The phagocytic cells use a combination of degradative enzymes, antimicrobial peptides, and reactive oxygen species to kill the invading microorganisms. The inflammatory cells also degrade the necrotic tissue formed in consequence of the infection through secretary or internal enzymes. In addition, they release signaling molecules that trigger and inflammatory response and begin to marshal the forces of the adaptive immune system. Cells infected with viruses are recognized by macrophages through dead/dying cells, Toll-like receptors and defensins. These macrophages further respond by secreting inflammatory cytokines, hydrolyzing viral proteins in phagolysosomes and present the viral proteins at the nearby lymph nodes and spleen to activate more inflammatory cells. The complement system can also recognize the viruses, activate the inflammatory cells to kill the virus and further induce adaptive immune system to generate antibodies.

As discussed above, in the innate immune system, the inflammatory cells (neutrophils and macrophages) play the central role in the host defense against all kinds of infection, ranging from viruses and bacteria, single-celled fungi and protozoa, to large complex metazoan such as parasitic worms. The inflammatory cells actively seek, engulf and destroy pathogens directly or through a variety of cell-surface receptors such as Toll-like receptors and complement receptors. If a pathogen is too large such as large parasites, a group of macrophages and neutrophils will gather around the invader. Activated macrophages also recruit additional phagocytic cells to sites of infection. Inflammatory cells also secrete a variety of signaling molecules to mediate and amplify the inflammatory response. In the B cell-mediated adaptive immune response against infectious pathogens, newly generated antibody binds to the antigens on the pathogens through its Fab fragment and to the surface receptors (FcR) on the inflammatory cells (mainly macrophages) through its Fc fragment and therefore link the inflammatory cells to pathogens and further kill them.

Based on the disclosed discovery, the administration of plasminogen and its derivatives plays a pluripotent role in protecting against e.g. *S. aureus*-induced bacterial arthritis, open wound infection and otitis media by activating inflammatory cells, killing bacteria, removing necrotic tissue, enhancing cytokine expression and promoting normal tissue remodeling. All these effects are different aspects of the potent functions that inflammatory cells exert against all kinds of infections. A working hypothesis has been developed in order to explain all the data we have. In this hypothesis, the key point is that plasminogen potentiates the activity of inflammatory cells and therefore mediates the processes such as killing bacteria, removing necrotic tissue, enhancing cytokine expression and promoting normal tissue remodeling. As indicated above, the inflammatory cells (neutrophils and macrophages) play the central role in the host defense against all kinds of infection, ranging from viruses and bacteria, single-celled fungi and protozoa, to large complex metazoan such as parasitic worms. Therefore, discoveries reported in the current invention support the conclusion that plasminogen and its derivatives are novel drug candidates in host defense against all the infectious diseases and necrosis.

Examples of this invention have been shown in order to demonstrate the potent anti-infectious roles of the plasminogen-activator system from different angles and in different models. Example 1 demonstrates that plg−/− mice have much more severe tissue destruction and more severe chronic inflammation as compared to plg+/+ mice after the induction of bacterial arthritis. These plg−/− mice also have impairment in killing bacteria (Example 3) and lower levels of IL-10 expression (Example 9), but the infiltration of the infected joints by macrophages and neutrophils is not overtly impaired in plg$^{-/-}$ mice (Example 4). Antibiotic treatment kills bacteria and reduces inflammation, but does not decrease formation of necrotic tissue in plg$^{-/-}$ mice (Example 2). However, systemic or local supplementation of plg$^{-/-}$ mice with human plasminogen (hPlg) restored the normal host defense against *S. aureus*-induced bacterial arthritis (Examples 5 & 6) and increased the IL-6 protein expression in the infected knee joints (Example 8). Local supplementation of plg$^{+/+}$ mice with human plasminogen enhances the host defense against *S. aureus* infection (Example 7), which strongly indicate that plasminogen is an excellent anti-infection agent superior than antibiotics and can be used effectively on wild-type normal animals. The importance of the plasminogen-activation system in host defense and tissue remodeling against infection is further demonstrated by the use of uPA−/− mice (Example 10). Example 10 shows that factors that activate plasminogen can also be useful as a therapeutic since plasminogen appears to be less effective in the absence of an activator. Furthermore, the essential roles of plasminogen in the host defense against infection were further confirmed by the use of plg−/− mice in another bacterial arthritis model (i.v. injection of bacteria, Examples 11 & 12) and another two open-wound infection models, incisional wound (Example 13) and scald burn wound (Example 14). Investigation of the spontaneous development of otitis media indicate that all of the plg−/− mice studied have ear infection whereas all of the plg+/+ mice remained uninfected (Example 17). Bacterial recovery from the ear tissues demonstrated that only 1 type of bacteria identified in 1 out of 6 plg+/+ mice, whereas 4 types of bacteria identified in 5 out of 6 plg−/− mice (Examples 15 & 16). Overall these examples have characterized the pluripotent roles of plasminogen from various anti-infectious aspects and strongly support the conclusion that plasminogen and its derivatives are novel drug candidates in host defense against all the infectious diseases.

Since plasminogen compounds and methods of the present invention provide an inflammatory response directed to infection or necrotic conditions, the compounds and methods of the present invention may provide a defense against all infectious disease, especially bacterial infectious disease, and necrosis. Such infection conditions include infectious diseases and other diseases where tissue infection is commonly observed, for instance during infection defense, chronic ulcers and diabetic ulcers. Such necrosis exist not only in the disease model hereby studied, but also other types of diseases which can also induce tissue necrosis, such as avascular femoral head necrosis, papillary necrosis, hip osteonecrosis, renal cortical necrosis, acute tubular necrosis, acute retinal necrosis, acute tubular necrosis, myocardial infarction, pancreatic necrosis, ischemic colitis, necrotizing fasciitis. There are many causes of necrosis including injury, infection, cancer, infarction, invenomation, slow and non-healing wounds, diabetes and inflammation. In addition, it was discovered that severe inflammation, tissue destruction, necrosis and bacterial growth all permanently persisted in plasminogen-deficient animal, therefore offering a novel model for studying bacterial infection and tissue necrosis, and screening methods for identifying and evaluating drugs and treatment methods for enhancing bacterial infection and tissue necrosis.

Accordingly, in a first aspect the invention refers to the use of a compound that is a component of the plasminogen-activating pathway or a compound having the capacity to activate plasminogen either directly or indirectly via activating an upstream component of the plasminogen-activating pathway for the manufacture of a pharmaceutical composition for the prophylaxis, prevention and/or treatment of infectious disease.

In a preferred embodiment the component of the plasminogen-activating pathway is selected from plasminogen, human recombinant plasmin, Lys-plasminogen, Glu-plasminogen, plasmin, variants and analogues of plasminogen and plasmin comprising one or more of the kringle and protease domains of plasminogen and plasmin, mini-plasminogen, mini-plasmin, plasminogen activators, tPA and uPA.

In another preferred embodiment the compound with the capacity to activate plasminogen is selected from streptokinase, saruplase, alteplase, reteplase, tenecteplase, anistreplase, monteplase, lanoteplase, pamiteplase, staphylokinase and recombinant forms and variants of the components of the plasminogen-activating pathway.

In general, the component of the plasminogen-activating pathway or the compound with the capacity to activate plasminogen can be administered systemically, locally, topically, intravenously, intramuscularly, subcutaneously, via inhalation, intrathecally, via local injection, via intra-articular injection or per rectally. In a preferred embodiment, topical administration and/or local injection are used.

Also, the component of the plasminogen-activating pathway or the compound with the capacity to activate plasminogen can be administered in combination with a suitable polypeptide carrier such as albumin, gelatine, and the like and/or one or more stabilizing agent(s) such as a detergent, a cyclodextrin, a saccharide, dimethyl sulfoxide, glycerol, ethylene glycol, propylene glycol, an antioxidant, a metal chelator, an enzyme inhibitor and the like. Such additives can be used to improve the stability of the product in many ways, including by minimising adsorption/absorption, by reducing aggregation, by improving solubility, by reducing oxidation and by reducing degradation. Methods for devising a suitable carrier for a given protein are well known within the art.

Further, by way of example the component of the plasminogen-activating pathway or the compound with the capacity to activate plasminogen may be administered at a dose of 0.0001 to about 1 g, preferably 0.005 mg to about 100 mg, more preferably from about 0.05 to about 50 mg. The dose in mg is with relation to square centimeter infected area (i.e. mg/square centimeter infected area)

Moreover, the administration of the component of the plasminogen-activating pathway or the compound with the capacity to activate plasminogen may for example be repeated at least once, preferably at least every day.

In the context of the present invention and the claim scope the subject can be any mammal subject, especially a human subject.

Also, in another preferred embodiment the infectious disease is a bacterial infectious disease.

Especially, the bacterial infectious disease is selected from otitis media, bacterial arthritis, gingivitis, periodontitis, conjunctivitis, keratitis, wound infection, surgical wound infections, virginal infections/injuries, necrosis, infections such as pneumonia, injuries in the respiratory organs caused by burns and/or infections and infected chronic leg ulcers in patients suffering from diabetes, systemic infections, infections due to venous or combined venous/arterial insufficiency or infectious arthritis or the like, infections secondary to the injuries in the joint tissues caused by infections Especially, as illustrated by the appended examples, the invention is effective for treating otitis media, bacterial arthritis, burn-related infection and incisional wound-related infection.

*Staphylococcus aureus* is the microorganism most frequently associated with bacterial arthritis, which results in synovial inflammation, cartilage and bone destruction, and eventually joint deformity.

Bacterial arthritis is a rapidly progressive and highly destructive joint disease in humans All destructive joint diseases, including inflammatory disorders such as rheumatoid arthritis, are connected to an increased incidence of bacterial arthritis. Certain forms of therapy such as joint implants and immunosuppressive treatment display an increased frequency of bacterial arthritis. *S. aureus* is the causative agent in about 60% of nongonococcal bacterial arthritis cases. In patients with rheumatic diseases, this value is even higher, approaching 75%. Laboratory models of bacterial arthritis have been used previously. In most instances bacteria have been injected intra-articularly. Morbidity and mortality due to *S. aureus* infections in the joints remain high despite the use of newer antibiotics. The increase in prevalence of multiantibiotic resistance in *S. aureus* is a major public health concern. Therefore, a novel, potent agent that can significantly increase the host defense is in great need.

Otitis media is the most common childhood disease except for common cold. The most important etiological factor related to otitis media is bacterial or viral infections of the upper respiratory tract. Otitis media is generally benign and a self-limiting disease, but despite this, the prescription rate of antibiotics is high. In fact, effects of antibiotics in curing otitis media lack evidence and so far surgical intervention is the therapy of choice for the treatment of recurrent acute otitis media (AOM) and otitis media with effusion (OME).

It is well known that the immediate colonization by the patient's normal skin flora (i.g. *S. aureus* and *Streptococcus pyogenes*) occurs following injury. Especially after the introduction of penicillin G in the early 1950s, which resulted in the virtual elimination of *Streptococcus pyogenes* as a cause of infection in thermally injured patients, *S. aureus* became the principal etiological agent of wound infection. Therefore *S. aureus* is one of the most common bacterium species on open-wound infection. Incisional wounds and burn wounds are the most common wound types observed in clinical practice. Similar to the situation in bacterial arthritis, due to the increasing problem of drug resistance of bacteria, a novel, potent agent that can significantly increase the host defense is in great need.

Basically, the invention is effective for treatment of all infectious diseases including infectious diseases induced by bacterial, viral and fungal infections.

Basically, since plasminogen compounds and methods of the present invention provide an inflammatory response directed to infection or infectious disease or necrotic conditions, the compounds and methods of the present invention may provide an effective treatment of all infectious diseases, particularly infectious diseases induced by bacterial, viral and fungal infections.

Bacterial and fungal agents that can cause infectious disease or symptoms and that can be treated according the present invention include, but are not limited to, the following Gram-Negative and Gram-positive bacteria, bacterial families, and fungi: *Actinomyces* (e.g., *Norcardia*), *Acinetobacter, Cryptococcus neoformans, Aspergillus*, Bacillaceae (e.g., *Bacillus anthrasis*), *Bacteroides* (e.g., *Bacteroides fragilis*), Blastomycosis, *Bordetella, Borrelia* (e.g., *Borrelia burgdorferi*), *Brucella, Candidia, Campylobacter, Chlamydia, Clostridium* (e.g., *Clostridium botulinum, Clostridium dificile, Clostridium perfringens, Clostridium tetani*), *Coccidioides, Corynebacterium* (e.g., *Corynebacterium diptheriae*), *Cryptococcus, Dermatocycoses, E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Salmonella typhi*), *Serratia, Yersinia, Shigella*), *Erysipelothrix, Haemophilus* (e.g., *Haemophilus influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Neisseriaceae (e.g., *Neisseria gonorrhea, Neisseria meningitidis*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Staphylococcus* (e.g., *Staphylococcus aureus*), *Menin-*

*giococcus, Pneumococcus* and *Streptococcus* (e.g., *Streptococcus pneumoniae* and Groups A, B, and C Streptococci), and Ureaplasmas.

These bacterial, parasitic, and fungal families can cause diseases or symptoms, including, but not limited to: Sepsis such as bacteremia, hemorrhagic septicemia; and fungemia; Central nervous system bacterial infections such as Lyme neuroborreliosis, bacterial meningitis and encephalitis, cerebral toxoplasmosis and neurosyphilis; Bacterial eye infections, such as bacterial conjunctivitis, infectious keratoconjunctivitis, infectious keratitis, ocular tuberculosis, and uveitis; Bacterial ear infections such as otitis media, external otitis; Sexually transmitted diseases such as *Chlamydia* infections, gonorrhea, and syphilis; Infectious skin diseases such as cellulitis, dermatomycoses, and bacterial skin diseases such as actinomycosis, angiomatosis, eethyma, erysipelas, staphylococcal skin infections, cutaneous syphilis, and cutaneous tuberculosis; Bacterial vaginosis; Respiratory tract infections such as whooping cough and pneumonia such as pneumococcal pneumonia, staphylococcal pneumonia and *mycoplasma* pneumonia; Urinary tract infections such as bacteriuria; Wound infections such as surgical wound infections, chronic infected skin ulcers, necrosis, open-wound infections; Bacterial arthritis; Infectious bone diseases such as osteitis, osteomyelitis, periostitis, spondylitis, and osteoarticular tuberculosis; Cardiovascular infections such as bacterial endocarditis, cardiovascular syphilis, and cardiovascular tuberculosis; Periodontal diseases such as gingivitis and periodontitis; AIDS-related opportunistic infections; Pelvic infections; Infectious pregnancy complications; which accordingly can be treated according to the present invention. For a more extensive listing of infectious diseases for which the invention would be effective, reference is made to the webpage http://www.health.vic.gov.au/ideas/diseases/quicklinks.htm, or to any relevant review journal in the art disclosing infectious diseases (see reference list).

Since plasminogen-activating pathway and compounds of the present invention provide an inflammatory response to viral infections in a similar manner as for bacterial infections and necrotic conditions, the compounds and methods of the present invention provide a similarly useful defense against viral infections and conditions including those listed below.

Viral agents that can cause infectious disease or symptoms and that can be treated according to the present invention include, but are not limited to, Arbovirus Infections, such as Bluetongue, Dengue, Arbovirus Encephalitis, Phlebotomus Fever, Rift Valley Fever, Tick-Borne Diseases, and Yellow Fever; Viral Bronchiolitis; Central Nervous System Viral Diseases, such as Encephalitis, Viral Meningitis, Myelitis, Poliomyelitis, and Pseudorabies; DNA Virus Infection, such as Adenoviridae Infections, African Swine Fever, Circoviridae Infections, Hepadnaviridae Infections, Herpesviridae Infections including but not limited to Herpes Simplex, Herpes Zoster, and Cytomegalavirus Infections, Papillomavirus Infections, Parvoviridae Infections, Polyomavirus Infections, and Poxyiridae Infections; Viral Encephalitis, such as Arbovirus Encephalitis, Herpes Simplex Encephalitis, and Varicella Zoster Encephalitis, Viral Eye Infections, such as viral Conjunctivitis, Cytomegalovirus Retinitis, Herpes Zoster Ophthalmicus, and Herpetic Keratitis; Viral Hepatitis, such as Hepatitis A, Hepatitis B, Hepatitis C, Hepatitis D, and Hepatitis E; Opportunistic Infections, such as AIDS-Related Opportunistic Infections; Viral Pneumonia; RNA Virus Infections, such as Arenaviridae Infections, Astroviridae Infections, Birnaviridae Infections, Bunyaviridae Infections including but not limited to Hantavirus Infections, Caliciviridae Infections, Arbovirus Encephalitis, Flaviviridae Infections, Viral Hemorrhagic Fevers, Mononegavirales Infections including but not limited to Rhabdoviridae Infections such as Rabies, Paramyxoviridae Infections such as Morbillivirus infection including but not limited to measles, Pneumovirus Infections including but not limited to Respiratory Syncytial Virus Infection, and Rubulavirus Infections including but not limited to mumps, Nidovirales Infections including but not limited to Coronavirus Infections such as Severe Acute Respiratory Syndrome, Orthomyxoviridae Infections, such as influenza, Picornaviridae Infections, such as enterovirus infections, Reoviridae Infections including but not limited to Rotavirus Infections, Retroviridae Infections including but not limited to Lentivurs Infections, and Togaviridae Infections; Viral Sexually Transmitted Diseases; Viral Skin Diseases, such as Erythema Infectiosum, Exanthema Subitum, Herpes Simplex, Molluscum Contagiosum, and Warts; Slow Virus Diseases, such AIDS, Progressive Multifocal Leukoencephalopathy, and Subacute Sclerosing Panencephalitis; Tumor Virus Infections, such as Epstein-Barr Virus Infections, Marek Disease, and Papillomavirus Infections, and Viremia.

In another embodiment, the composition comprises a combination of two or more compounds which are components of the plasminogen-activating pathway or compounds with the capacity to activate plasminogen.

In yet another embodiment, the composition further comprises at least one antibiotic agent.

The antibiotic agent is e.g. selected from the group consisting of tetracyclines, amphenicols, beta-lactams, penicillins, sulphonamides, macrolides, lincosamides, streptogamins, streptomycins, quinolones and metronidazoles, as well as any proper antibacterial agent, mycocide or fungicide.

Further, in yet another embodiment, the prophylaxis, prevention and/or treatment of infectious disease comprises inducing an immune response against an infectious pathogen.

In a second aspect, the invention relates to a method for the prophylaxis, prevention and/or treatment of infectious disease, which comprises administering a pharmaceutical composition comprising an effective amount of a compound which is a component of the plasminogen-activating pathway or a compound with the capacity to activate plasminogen to a subject in need of such treatment.

In still another aspect the invention relates to a pharmaceutical composition for the prophylaxis, prevention and/or treatment of infectious disease comprising an effective amount of a compound which is a component of the plasminogen-activating pathway or a compound with the capacity to activate plasminogen, and a pharmaceutically acceptable carrier.

In yet another aspect, the invention relates to a kit of parts for use in the prophylaxis, prevention and/or treatment of infectious disease comprising an effective amount of a compound which is a component of the plasminogen-activating pathway or a compound with the capacity to activate plasminogen and at least one antibiotic, antiviral or antimycotic agent, in separate vials In a further aspect, the invention relates to a method of identifying an agent that is useful in promoting host defense against infection, comprising the steps of: (a) administering a test agent to an animal having a bacterial arthritis; (b) evaluating at least one of the following parameters: (i) the extent of killing bacteria, (ii) necrotic tissue formation, (iii) inflammatory cell activation, (iv) cytokine expression of the infection e.g. bacterial arthritis by using fluorescent or radio-isotopic biomarker labels, microbiological plaque assay from body fluid or tissue homogenates, FACs analysis, ELISA, histological examinations, and/or cytotoxicity assay (for killing bacteria, one can simply recover bacteria from one tissue/ organ, for necrotic tissue formation, one can quantify tissue autopsy, for inflammatory cell activation, one can determine histochemically, ELISA, western blotting of different inflammatory cell markers and for cytokine expression, there are kits for the detection of the levels of cytokines. All of these methods are included in the Example section of this disclosure which can be used); (c) comparing the chosen parameter(s) of step (b) with a control value, wherein plasminogen can be used as a positive control and a non-treated group as a negative control); and (d) selecting any test agent for which the chosen parameter(s) is(are) more beneficial compared to the control value as an agent useful in promoting host defense against infection.

In a preferred embodiment, the test of model animal is selected from a member of the group consisting of a wild-type animal and a transgenic animal lacking endogenous expression of plasminogen.

In yet another aspect, the invention refers to a method for diagnosis of an ongoing infection, comprising determining the diagnostic presence of plasminogen.

In still another aspect, the invention relates to a kit for use in the determination of plasminogen in a sample from a patient, wherein the sample is from body fluids, serum, excreted waste products, such as urine or faeces, exhalation air, or the like, in order to determine an ongoing infection and/or the effect of an ongoing treatment, comprising a plasminogen determinant and means for collecting, storing and/or examining the patient sample.

Accordingly, the present invention provides for a method of improving host defense against infection, comprising administering a composition comprising an active agent which is a component of the plasminogen-activation pathway or a compound with the capacity to activate plasminogen. Preferably, the active agent is selected from plasmin or plasminogen or an analogue of plasmin or plasminogen. Most preferably, the active ingredient is plasminogen. The active agent can be administered by any route of administration known in the art. Preferred, non-limiting, routes of administration include topical application and local injection. The agent may also be present in a wound dressing applied onto the infected area, if possible, from which it is transferred to the infected site. The agent may also be present in a rinsing solution, eye drops and gargling solution or the like, applied to clean the infected area.

The invention also provides for a method of initiating the host defense against infection in conditions where infection host defense is retarded or impaired, comprising administering an active ingredient which is plasmin or plasminogen. In a particular embodiment, the method of the invention can be used for improving infection defense in conditions of local or systemic low levels of plasmin or plasminogen. Such conditions may be congenital and/or acquired.

Examples of congenital conditions with systemic deficiency of plasmin or plasminogen include but are not limited to mutations in the plasminogen (PLG) gene (GenBank Reference Sequence accession No: NM_000301, GeneID:5340; the amino acid residue numbers herein refer to the mature human peptide as defined in GenBank accession No: NP 000292) resulting in dysplasminogenias such as ALA601THR, VAL355PHE, SER572PRO AND GLY732ARG, or in type I plasminogen deficiency such as ARG216HIS, TRP597TER, GLU460TER, LYS212DEL and LYS19GLU. In cases where congenital plasminogen deficiency is present, administering a drug which is plasminogen is preferred.

Examples of acquired systemic and/or local defects of plasmin or plasminogen can be due to changes in physiologic states such as pregnancy, old age, stress, obesity, and temperature alterations. Various disease states, surgery, radiation, and diet can also trigger mechanisms leading to impaired fibrinolytic states. Several drugs, including anticancer agents, oral contraceptives, cytokines, and blood components can also produce transitory fibrinolytic deficit which can predispose patients to thrombotic complications. The identification of the patient populations with an impaired fibrinolytic state is an important step toward the prevention of thrombotic complications which may lead to such catastrophic events as myocardial infarction and thrombotic strokes. Both functional and immunologic methods have currently become available for the rapid diagnosis of fibrinolytic deficit. Thus, it is important to evaluate patients who are at risk of thrombotic complications due to fibrinolytic deficit.

In another embodiment, the invention provides a method for treatment of infection and enhancement of infection defense in human or non-human subjects by administering a compound or drug which is plasminogen, plasmin, an activator of plasminogen, or a compound enhancing the proteolytic activity of plasmin.

In addition, the invention provides for a method of improving infection defense against bacterial arthritis and/or otitis media, comprising administering a composition comprising an active ingredient which is a component of the plasminogen activation pathway or a compound with the capacity to activate plasminogen. In a preferred embodiment, the active ingredient is plasminogen, and the composition administered via local application.

Moreover, the invention provides for a method for reducing or preventing necrosis formation by administering a composition comprising local or systemic administration of a composition comprising a compound which is a component of the plasminogen activation pathway or a compound with the capacity to activate plasminogen. The composition may be part of a gel, lotion, balm, paste, wound bandage, or wound dressing. Alternatively, the composition may be administered systemically. In one embodiment, the method of the invention is applied in conjunction with plastic surgery to reduce the occurrence and the formation of infection, ulcer and necrosis.

In yet another embodiment, the invention provides for a method for treatment of infection and enhancement of infection defense in subjects with defects in plasmin-plasminogen system activity by administering a compound or drug which is plasminogen, plasmin, an activator of plasminogen, or a compound enhancing the proteolytic activity of plasmin.

The invention further provides for a method of identifying a compound useful for improving infection defense in an animal model. According to the method of the invention, an infection is inflicted upon a plasminogen-deficient animal, and the test compound administered to the animal via a predetermined route. Infection defense in the plasminogen-deficient animal is then compared to a control value such as, e.g., infection defense in a wild-type animal, to evaluate whether the test compound improved the rate of infection defense or reduced necrosis formation. One animal model preferred for this method is knock-out mice lacking one or both alleles of plasminogen, or transgenic mice. In one embodiment, the knee joints are infected, and the host defense of the joints is studied in the presence and absence of added plasminogen. In another embodiment, the spontaneous development of otitis media is followed. The gross appearance of the TM was carefully examined and documented under an otomicroscope, and the host defense of the TMs is studied in the presence and absence of added plasminogen. In yet another embodiment, an open wound, for instance burn and incisional wounds, is infected and the host defense against infection at the wounded site is studied in the presence and absence of added plasminogen.

Furthermore, the invention provides for a method for in vivo screening for drugs that can be used for improving host defense against infection comprising an in vitro or in vivo model in which plasminogen is expressed. The in vivo model comprises an animal that is wild-type or plasminogen-deficient. After administration of one or more drugs to be screened, the activity or levels of plasminogen and/or plasmin will be measured. In a preferred embodiment, the animal model is a bacterial arthritis model in the knee joints, and bacterial arthritis is induced before, in conjunction with, or after the administration of the drug. In another embodiment, the animal model is open-wound infection model and the open-wound infection is induced before, in conjunction with, or after the administration of the drug.

The invention also provides for a method for improving host defense against infectious diseases, by administering a composition comprising an activator of plasminogen activity, or a compound mimic of plasminogen expression. Preferably, plasminogen is administered locally to attain a high concentration in the infected area. In another embodiment, the composition comprises a compound that mimics plasminogen/plasmin activity and molecules with similar activity. In still another embodiment, the composition comprises a drug which up-regulates the expression of plasminogen.

Additionally, the invention provides for a method of treating a chronic infection and necrosis by administering a drug that up-regulates the expression of plasminogen or plasminogen-activators.

Still further, the invention refers to the use of a compound of the group comprising: plasminogen, plasmin, a fragment of plasminogen or plasmin, a component of the plasminogen activation pathway, a plasminogen analogue, a plasmin analogue, or an analogue of a component of the plasminogen activation pathway, or a compound with the capacity to activate plasminogen for the manufacture of a medicament for promoting host defense of bacterial arthritis and otitis media and open wound infection, and/or for removing necrotic tissue and/or for improving host defense against infection and/or for reducing necrotic tissue formation in a healing wound.

BRIEF DESCRIPTION OF THE DRAWINGS

The above features and many other advantages of the invention will become better understood by reference to the following detailed description when taken in conjunction with the accompanying drawings.

DEFINITIONS

Figure 1:
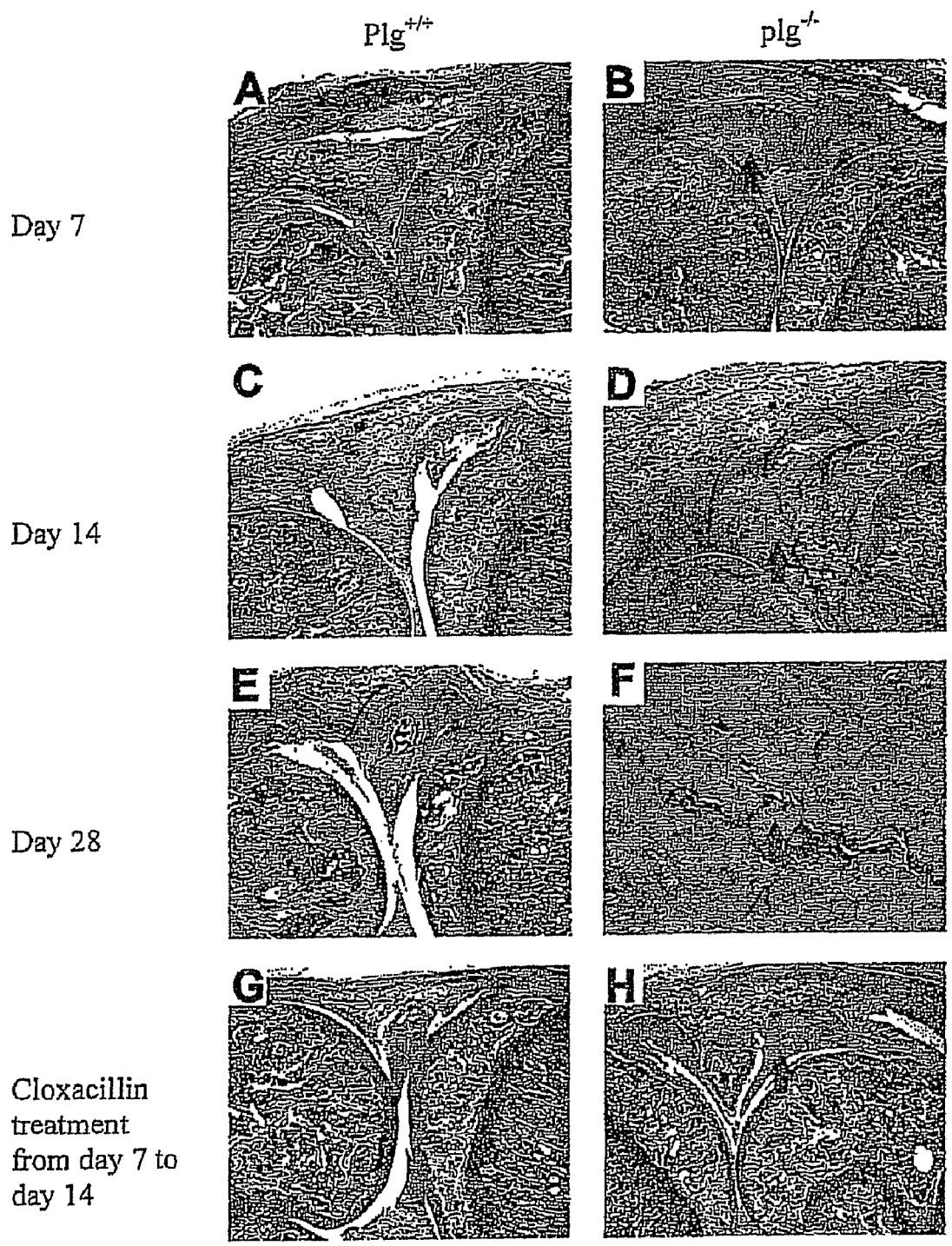
FIG. 1A-H. Histologies of representative sections of arthritic knee joints from plg$^{+/+}$ (left) and plg$^{-/-}$ (right) mice. Plg$^{+/+}$ and plg$^{-/-}$ mice were given an intraarticular injection of 1×10$^6$ CFU S. aureus. (A, C, E): Arthritic knee joints from plg$^{+/+}$ mice at days 7, 14, and 28, respectively, after arthritis induction. (B, D, F): Arthritic knee joints from plg$^{-/-}$ mice at days 7, 14, and 28, respectively, after arthritis induction. (G): Arthritic knee joints from plg$^{+/+}$ mice 7 days after antibiotic treatment. (H): Arthritic knee joints from plg$^{-/-}$ mice 7 days after antibiotic treatment. Necrotic tissue is observed in the joint cavity (arrow). Synovial membrane (Sm).

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

"A compound of the group comprising: plasminogen, plasmin, a component of the plasminogen activation pathway, a plasminogen analogue, such as mini-plasmin, a plasmin analogue, an analogue of a component of the plasminogen activation pathway, a plasminogen activator" refers to a compound that directly or indirectly provides the effect of plasminogen or plasmin, respectively.

"A component of the plasminogen activation pathway" refers to plasminogen, Lys-plasminogen, Glu-plasminogen, variants and analogues of plasminogen comprising one or more domains of plasminogen such as one or more of the kringle domains and the proteolytic domain exemplified by mini-plasminogen; plasmin and variants and analogues of plasmin comprising at least one or more domains of plasmin such as one or more of the kringle domains and the proteolytic domain, exemplified by mini-plasmin and delta-plasmin; a plasminogen activator having the final effect of activating plasminogen, e.g. by a cascade of events resulting in the formation or activation of plasminogen exemplified by uPA and tPA and variants and analogues of tPA and uPA comprising one or more domains of tPA or uPA such as one or more of the kringle domains and the proteolytic domain. Variants of plasminogen, plasmin, tPA and uPA include all naturally occurring genetic variants of human as well as other mammalian forms of these proteins, as wells as mutant variants of these proteins obtained by conservative amino acid replacements. An "analogue" of plasminogen or plasmin is a compound providing essentially an analogous effect as plasminogen or plasmin, respectively, as measured by enzymography, ELISA (enzyme-linked immunosorbent assay) and FACS (fluorescence activated cell sorter), There is also an assay for measuring levels of converted plasmin activity as described previously: Ny, A., Leonardsson, G., Hagglund, A. C., Hagglof, P., Ploplis, V. A., Carmeliet, P., and Ny, T. (1999). Ovulation in plasminogen-deficient mice. Endocrinology 140, 5030-5035.). An "analogue" of a component of the plasminogen activation pathway is a compound providing essentially an analogous effect as a component of the plasminogen activation pathway as measured by the levels of plasmin activity that this analogue activates.

"Necrosis" refers to death of tissue in the body. This happens when not enough blood is supplied to the tissue, whether from injury, radiation, or chemicals. Necrosis is not reversible. There are many causes of necrosis including injury, infection, cancer, infarction, invenomation, chronic wounds, ulcers and inflammation.

"Topical" and "topical application" refer to non-systemic, local, administration of an active ingredient. Thus, topical application can refer to application of an active ingredient to the external surface of the interesting area.

"Local injection" refers to non-systemic, local administration of an active ingredient into the tissue of/nearby the interested area.

"Intra-articular injection" refers to local administration of an active ingredient into the joint space between two connecting bones.

"Infectious diseases" and "infection" refers to the detrimental colonization of a host organism by a foreign species. In an infection, the infecting organism seeks to utilize the host's resources to multiply (usually at the expense of the host). The infecting organism, or pathogen, interferes with the normal functioning of the host and can lead to chronic wounds, gangrene, loss of an infected limb, and even death. The host's response to infection is inflammation. Colloquially, a pathogen is usually considered a microscopic organism, the most familiar are viruses and bacteria. Other infectious pathogens are viroids and eukaryotic organisms, ranging from single-celled fungi and protozoa, through large complex metazoan such as parasitic worms.

The "activity" of a protein or compound refers to the effect that the protein or compound has on a specific reaction, and is a measure of its ability to affect, modulate, participate in, or promote the reaction. Generally, the activity of a protein or other compound can be measured. For example, in the case of enzymes such as plasmin, PA, and MMPs, and modulators enzyme activity can be expressed as the rate at which the product of the reaction is produced, represented, e.g., as the amount of product produced per unit of time and of enzyme (e.g., concentration or weight). In the case of modulators such as PAI-1 or uPA, activity can refer to the ability of the modulator to inhibit or promote, increase or decrease, up- or downregulate, the rate of a reaction or the amount of product formed from the reaction.

A "wound" is a break in the structure of an organ or tissue, including epithelium, connective tissue, and muscle tissue, caused by an external agent. Examples of wounds include, but are not limited to, bruises, grazes, tears, cuts, punctures, and burns. A particular type of wounds are those that are a consequence of plastic surgery procedures.

"Otitis media" is defined as inflammatory conditions of the ear. Otitis media, including acute otitis media (AOM) and otitis media with effusion (OME), is the most common childhood disease except for common cold (5). The most important etiological factor related to otitis media is bacterial or viral infections of the upper respiratory tract. The biochemical composition of the middle ear effusions in otitis media reflects inflammatory changes in the middle ear mucosa. The fluid is a mixture of transudates and secretory products from glands as well as products from inflammatory cells and bacteria.

"Treatment" of a subject, or "treating" a subject for a disease or condition herein means reducing or alleviating clinical symptoms of the disease or condition such as impaired or slow wound-healing.

"Enhancing" wound healing means increasing the speed by the which the wound heals. Alternatively, "enhancing" wound healing means reducing the formations of scar tissue during or after healing.

A "subject" herein includes both human and non-human animals. Non-human animals include, without limitation, laboratory animals such as mice, rats, rabbits, hamsters, guinea pigs, etc.; domestic animals such as dogs and cats; and farm animals such as sheep, goats, pigs, horses, and cows. A non-human animal of the present invention may be a mammalian or non-mammalian animal; a vertebrate or an invertebrate.

A "control", "control value" or "reference value" in an assay is a value used to detect an alteration in, e.g., the healing of a skin wound, or healing of a perforated tympanic membrane, or any other assays described herein. For instance, when studying healing of a tympanic membrane perforation, the inhibitory/stimulatory effect of an agent can be evaluated by comparing the healing of a wound or perforation to that of a control. The control or reference may be, e.g., a predetermined reference value, or may be determined experimentally. In such an assay, for example, a control or reference may be the healing of a similar wound or perforation in an animal not exposed to the drug or active agent.

A subject "at risk for", "predisposed to", or "susceptible to" a disease or condition means that the risk for the individual to contract or develop the disease or condition is higher than in the average population.

A "deficiency" of a compound means that the amount, level, or concentration of the compound is significantly lower than a control value. For example, in a plasminogen-deficient animal, the body fluid and tissue levels of plasminogen is significantly lower than in a wild-type animal.

As used herein, "about" or "approximately" shall mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not. A "statistically significant" difference means a significance is determined at a confidence interval of at least 90%, more preferably at a 95% confidence interval.

Molecular Biology Definitions

In accordance with the present invention there may be employed conventional molecular biology, microbiology, and recombinant DNA techniques within the skill of the art. Such techniques are explained fully in the literature. See, e.g., Sambrook et al. (Molecular Cloning—A Laboratory Manual, Cold Spring Harbor Laboratory Press, 1989); Glover (DNA Cloning: A Practical Approach, Volumes I and II, 1985); Hames and Higgins (Nucleic Acid Hybridization, 1985); Hames and Higgins (Transcription And Translation, 1984); Freshney (Animal Cell Culture, 1986); Perbal (A Practical Guide To Molecular Cloning, 1984); and Ausubel et al. (Current Protocols in Molecular Biology, John Wiley & Sons, Inc., 1994).

If appearing herein, the following terms shall have the definitions set out below.

A "protein" or "polypeptide", which terms are used interchangeably herein, comprises one or more chains of chemical building blocks called amino acids that are linked together by chemical bonds called peptide bonds.

An "enzyme" means any substance, preferably composed wholly or largely of protein, that catalyzes or promotes, more or less specifically, one or more chemical or biochemical reactions. The term "enzyme" can also refer to a catalytic polynucleotide (e.g. RNA or DNA). A "test" enzyme is a substance that is tested to determine whether it has properties of an enzyme.

A "native" or "wild-type" protein, enzyme, polynucleotide, gene, or cell, means a protein, enzyme, polynucleotide, gene, or cell that occurs in nature.

A "mutant", "altered", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. An alteration in a gene includes, but is not limited to, alteration the promoter region, or other regions which affect transcription, which can result in altered expression levels of a protein. A mutant or modified protein or enzyme is usually, although not necessarily, expressed from a mutant polynucleotide or gene.

A "mutation" or "alteration" means any process or mechanism resulting in a mutant protein, polynucleotide, gene, or cell. This includes any mutation in which a protein, polynucleotide, or gene sequence is altered, any protein, polynucleotide, or gene sequence arising from a mutation, any expression product (e.g. protein) expressed from a mutated polynucleotide or gene sequence, and any detectable change in a cell arising from such a mutation.

"Function-conservative variants" are proteins or enzymes in which a given amino acid residue has been changed without altering overall conformation and function of the protein or enzyme, including, but not limited to, replacement of an amino acid with one having similar properties (such as, for example, acidic, basic, hydrophobic, and the like) "conservative amino acid replacements". Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

The Plasminogen-Activation System

Plasmin is the key component of the PA system. It is a broad-spectrum protease which has the ability to degrade several components of the ECM including fibrin, gelatin, fibronectin, laminin and proteoglycans (6). In addition, plasmin can convert some pro-matrix metalloproteinases (pro-MMPs) to active MMPs. It has therefore been suggested that plasmin may be an important upstream regulator of extracellular proteolysis. Plasmin is formed from the zymogen plasminogen through proteolytic cleavage by either of two physiological PAs, tPA or uPA. As plasminogen is present in plasma and other body fluids at relatively high levels, the regulation of the PA system occurs mainly at the level of synthesis and activity of the PAs. Synthesis of the components of the PA system is highly regulated by different factors such as hormones, growth factors and cytokines. In addition, there exist specific physiological inhibitors of plasmin and PAs. The main inhibitor of plasmin is $\alpha_2$-antiplasmin (7). The activity of PAs is regulated by PAI-1, which inhibits both uPA and tPA, and PAI-2, which inhibits mainly uPA. Certain cells also have a specific cell-surface receptor for uPA (uPAR) that can direct proteolytic activity to the cell surface.

Plasminogen is a single-chain glycoprotein consisting of 791 amino acids (mature human peptide, GenBank Accession No: NP_000292) with a molecular mass of approximately 92 kDa (8; 9). Plasminogen is mainly synthesized in the liver and is abundant in most extracellular fluids. In plasma the concentration of plasminogen is approximately 2 µM. Plasminogen therefore constitutes a large potential source of proteolytic activity in tissues and body fluids.

Plasminogen exists in two molecular forms: Glu-plasminogen and Lys-plasminogen. The native secreted and uncleaved form has an amino-terminal (N-terminal) glutamic acid and is therefore designated Glu-plasminogen. However, in the presence of plasmin, Glu-plasminogen is cleaved at $Lys^{76}$-$Lys^{77}$ to become Lys-plasminogen. Compared to Glu-plasminogen, Lys-plasminogen has a higher affinity for fibrin and is activated by PAs at a higher rate. These two forms of plasminogen can be cleaved at the $Arg^{560}$-$Val^{561}$ peptide bond by uPA or tPA, resulting in the formation of the disulphide-linked two-chain protease plasmin. The amino-terminal part of plasminogen contains five homologous triple-loops, so-called kringles, and the carboxyl-terminal part contains the protease domain. Some of the kringles contain lysine-binding sites which mediate the specific interaction of plasminogen with fibrin and its inhibitor $\alpha_2$-AP. A novel and interesting finding is that a 38-kDa fragment of plasminogen, consisting of kringles 1-4, is a potent inhibitor of angiogenesis. This fragment is termed angiostatin and can be generated from plasminogen through proteolytic cleavage by several MMPs.

The main substrate for plasmin is fibrin, and dissolution of fibrin is pivotal for prevention of pathological blood clot formation (10). Plasmin also has substrate specificities for several other components of the ECM, including laminin, fibronectin, proteoglycans and gelatin, indicating that plasmin also plays an important role in ECM remodeling. Indirectly, plasmin can also degrade additional components of the ECM through its ability to convert some pro-MMPs to active MMPs, including MMP-1, MMP-2, MMP-3 and MMP-9. It has therefore been suggested that plasmin may be an important upstream regulator of extracellular proteolysis.

Models of Bacterial Arthritis to Study Infection

*Staphylococcus aureus* is the micro-organism that is most frequently associated with bacterial arthritis, which results in synovial inflammation, cartilage and bone destruction, and eventually joint deformity (11). Various animal species including mammals, birds and reptiles have been observed to develop spontaneous *S. aureus* arthritis and are therefore potential models for the induction of the disease. Considering the route of how the staphylococci spread through the body to reach the joints, which is an important trait, it has been clearly shown that the great majority of bacterial joint infections in humans are spread hematogenously. Thus, the optimal way to deliver live bacteria to provide a model of infection is via intravenous (i.v.) injection. On the other hand, the intra-articular route of bacterial inoculation bypasses the early stages of pathogenesis, and therefore provides a more defined model of bacterial arthritis. Thus in the present studies, the intra-articular way to deliver bacteria in order to better study the local bacterial growth, tissue destruction, necrotic tissue formation and inflammation has mainly been used as the model. However, we also performed a series of bacterial arthritis study using *S. aureus* via i.v. injection. Data obtained from both models have shown comparable results and both supported the conclusion that plasminogen/plasmin is essential in the host defense against *S. aureus*-induced bacterial arthritis.

It is well known that the immediate colonization by the patient's normal skin flora (i.e. *S. aureus* and *Streptococcus pyogenes*) occurs following injury. Especially after the introduction of penicillin G in the early 1950s, which resulted in the virtual elimination of *Streptococcus pyogenes* as a cause of infection in thermally injured patients, *S. aureus* became the principal etiological agent of wound infection. Therefore *S. aureus* is one of the most common bacterium species on open-wound infection. Incisional wounds and burn wounds are the most common wound types observed in clinical practice. Therefore, in the current patent application, the open-wound infection models we have used are infections by *S. aureus*, the principal etiological agent of wound infection, on burn and incisional wounds, the most common wound types in practice. Therefore, we consider the data obtained from these two open wound infection models give very important indication to the feasibility of applying the knowledge to the clinical situation.

EXAMPLES

The invention is further described by means of the following examples. However, these examples are only illustrative of the invention, and in no way limits the scope and meaning of the invention. Indeed, many modifications and variations of the invention will be apparent to those skilled in the art upon reading this specification, and can be made without departing from its sprit and scope.

Example 1

Persistent Inflammation and Tissue Destruction in plg$^{-/-}$ Mice During S. aureus-Induced Bacterial Arthritis This Example shows that plasminogen-deficient mice had persistent inflammation and tissue destruction compared to wild type control siblings. There are significantly more severe histopathological changes in plg$^{-/-}$ mice than in plg$^{+/+}$ mice during S. aureus-induced bacterial arthritis.

Methods

Mice. Plasminogen-heterozygous (plg$^{+/-}$) mice of a mixed genetic background (129×C57BL/6) were intercrossed to generate plg$^{+/+}$, plg$^{+/-}$ and plg$^{--}$ mice. Male plg$^{+/+}$ and plg$^{-/-}$ mice at 8-12 weeks of age were used for the experiments (Ploplis V A, Carmeliet P, Vazirzadeh S, Van Vlaenderen I, Moons L, Plow E F, Collen D: Effects of disruption of the plasminogen gene on thrombosis, growth, and health in mice. Circulation 1995, 92:2585-2593).

Induction of bacterial arthritis. Bacterial strain used in the study was S. aureus Phillips (Courtesy from Dr. Hook, Department of rheumatology and Clinical immunology, Gothenburg University, Sweden). Arthritis was induced by local injection of 1×10$^6$ colony-forming units (CFU) of S. aureus Phillips in 10 μl sterile PBS into the right knee joints of mice. As controls, the left knee joints were injected with 10 μl sterile PBS alone. Mice were sacrificed at different time points after inoculation and samples were taken to evaluate the severity of the disease. The Regional Ethical Committee of Umeå University approved all experimental protocols.

Histological analysis. At days 7, 14, and 28 after bacterial injection, mice were sacrificed and samples of whole knee joints were collected for histological analysis. In brief, knee joints were first fixed in 4% paraformaldehyde, embedded in paraffin, and thereafter 8-μm sections were prepared. Slides containing tissue sections were stained with Safranin-O for histological analysis. At least 10 knee joints were included in each experimental group.

Quantification of necrotic tissue in the infected joints. The images of the knee joints histological sections were taken with a Leica DC300F digital camera attached to a Leica DM LB microscope (Leica, Wetzlar, Germany). For determination of the amount of necrotic tissue in the infected joints, the images of entire knee joints histological sections were divided into 50×40 grids at ×50 magnification. Each square within the grid that contained the necrotic tissue was counted as a 'hit'. Three independent, randomly selected sections were counted from each joint and 5 joints from separate mice of the same genotype were used at each time point. Mean values of the 'hit' were calculated and shown.

Results

To study the effects of plasmin on the clinical outcome of bacterial arthritis, mice were injected with 1×10$^6$ CFU of S. aureus Philips in the knee joints. Thereafter, mice were sacrificed at different time points and the knee joints were dissected. Macroscopic examinations of knee joint samples from days 7, 14, and 28 after intra-articular injection revealed that plg$^{+/+}$ mice had similar levels of slight swelling in the knee joints. However, in plg$^{-/-}$ mice, the sizes of the bacterial injected knee joints increased during the whole experimental period. At day 28, the knee joints with bacterial injected were significantly enlarged, the joint cavities were filled with purulent material, and the synovial surfaces strongly bulged out.

Figure 2:
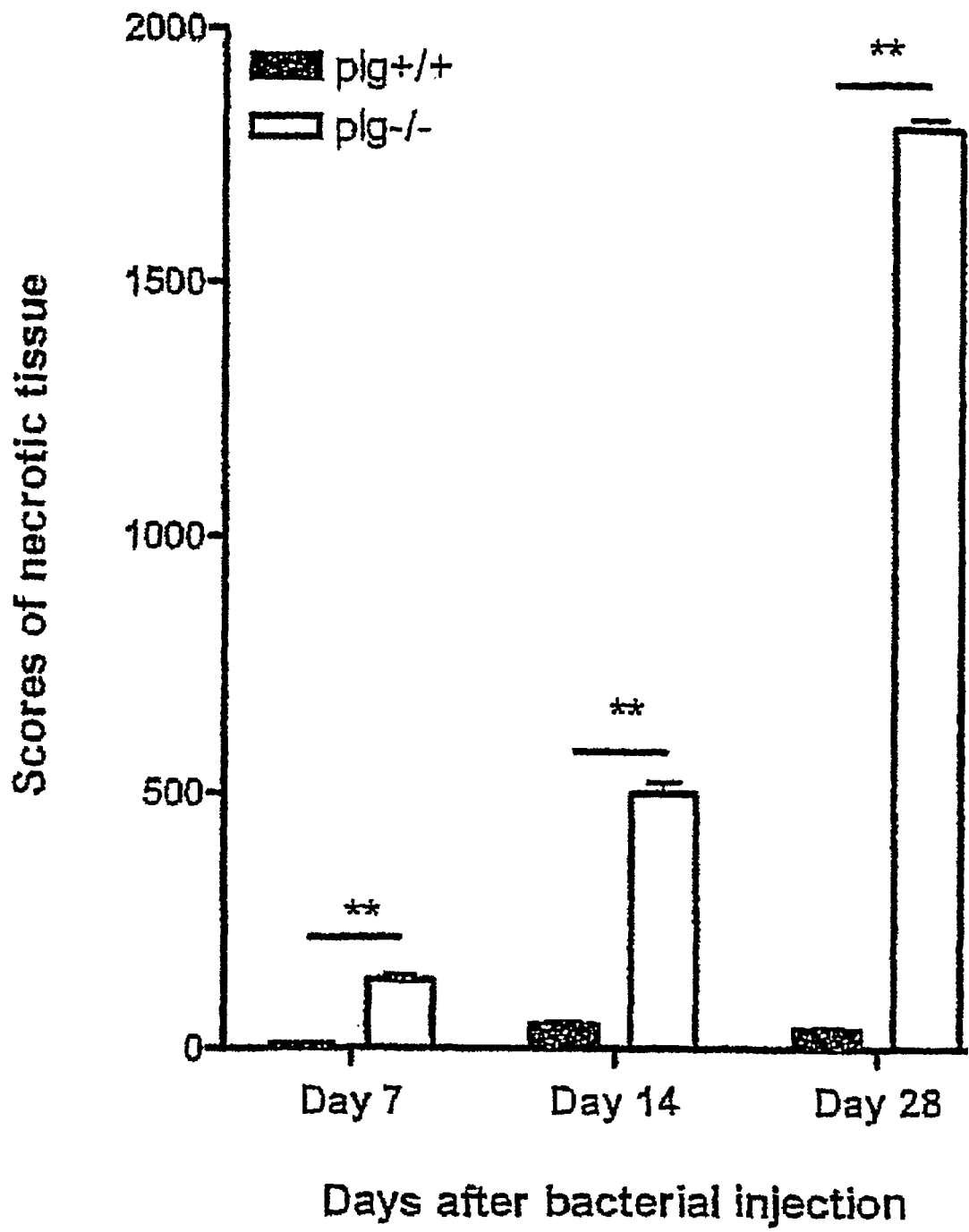
FIG. 2. Quantification of necrotic tissue in the infected joints at each time point. The amount of necrotic tissue in the infected joints was scored histologically, as described in Materials and Methods. Plg$^{+/+}$ and plg$^{-/-}$ mice were compared on day 7, day 14 and day 28 after 1×10$^6$ CFU of S. aureus injection. Results are expressed as mean±SD. **= $P<0.01$, by student t test.

The bacterial injected knee joints of plg$^{+/+}$ and plg$^{-/-}$ mice at days 7, 14 and 28 were prepared for histological analysis. As shown in FIG. 1, considerably more severe arthritis was observed in plg$^{-/-}$ mice than in plg$^{+/+}$ mice at all observation time points. At day 7 in plg$^{+/+}$ mice, inflammatory cells had infiltrated the joint cavity, the synovial membrane was thicker than normal, and the cartilage surface had been degraded (FIG. 1A, Sm). At day 14, inflammatory cells were observed adjacent to the eroded bone (FIG. 1C, arrow). However, at day 28, the number of inflammatory cells had declined and tissue repair of the damaged cartilage and bone had started (FIG. 1E). The disease development pattern was completely different in plg$^{-/-}$ mice. At day 7 in plg$^{-/-}$ mice, large amount of inflammatory cells had infiltrated the joint cavity, several parts of the bone were eroded, and necrotic tissue was observed (FIG. 1B). At day 14, the synovial membrane had become thicker than that at day 7, and the necrotic area had increased. Cartilage degradation and bone erosion were much more severe than at day 7 (FIG. 1D). At day 28, the whole knee joint was almost completely degraded, with only necrotic tissue and small parts of the cartilage remained (FIG. 1F). Semi-quantitative studies of the samples sections indicated that plg$^{-/-}$ mice had significantly higher levels of the tissue necrosis than that in plg$^{+/+}$ mice during whole disease development (FIG. 2). These data indicate that there are significantly more severe histopathological changes in plg$^{-/-}$ mice than in plg$^{+/+}$ mice during S. aureus-induced bacterial arthritis.

Example 2

Antibiotic Treatment Kills Bacteria and Reduces Inflammation, but does not Decrease Formation of Necrotic Tissue in plg$^{-/-}$ Mice Methods This experiment was performed in a similar manner as Example 1, except for administration of antibiotics to some of the animals.

Antibiotic treatment. The antibiotic cloxacillin (AstraZeneca, Södertälje, Sweden) was dissolved in sterile PBS and injected intraperitoneally into mice at a dosage of 0.5 mg/g body weight every 12-hour, starting at day 7 after bacterial injection. Mice were killed at day 14 after bacterial injection.

Results

The effects of antibiotic treatment on disease development in plg$^{+/+}$ and plg$^{-/-}$ mice were also investigated. Mice were injected with bacteria at day 0 and treated with cloxacillin twice per day from day 7 to day 14 after bacterial injection. Recovery of bacteria from the infected joints at day 14 indicated that the bacteria were completely killed in plg$^{-/-}$ mice after cloxacillin treatment (data not shown). Histopathological analysis revealed that the inflammation had subsided in plg$^{+/+}$ mice after antibiotic treatment (FIG. 1G) compared to mice that had not been treated with cloxacillin (FIG. 1C). In plg$^{-/-}$ mice treated with cloxacillin, the levels of inflammation were still higher than that in plg$^{+/+}$ mice with the same treatment. The cartilage and bone had largely been repaired (FIG. 1H). Noticeably, small areas of necrotic tissue remained in the synovium (arrow, FIG. 1H). These data reveal that intraperitoneal administration of cloxacillin successfully eliminated bacteria from knee joints, reduced tissue destruction and restored tissue repair processes in plg$^{-/-}$ mice. However, large area of necrotic tissue remained in the knee joints of plg$^{-/-}$ mice after the antibiotic treatment.

Example 3

Plasminogen Deficiency Impairs Bacterial Clearance

Methods

This experiment was performed in a similar manner as Example 1, except for the bacterial counts.

Bacterial counts. At days 2, 3, 4, 5, 7, 14, and 28 post bacterial injection, the knee joints were taken and homogenized in 1 ml sterile PBS. After serial dilutions, the solutions of homogenates were spreaded on LB agar plates and incubated at 37° C. overnight. Viable bacterial colonies were then counted to evaluate the number of bacteria in each homogenate.

Results

We then investigated the bacterial growth in the knee joints of $plg^{+/+}$ and $plg^{-/-}$ mice after bacterial arthritis induction. As shown in Table 1, in $plg^{+/+}$ mice, the quantity of S. aureus in the infected knee joints declined immediately from day 2 after bacterial injection. At day 7, S. aureus was undetectable in 50% (7/14) of the $plg^{+/+}$ mice. At day 14, S. aureus was undetectable in 80% (8/10) of the $plg^{+/+}$ mice, and less than $1\times10^3$ CFU was found in the other 2 mice. At day 28, the bacteria were completely eliminated in all $plg^{+/+}$ mice. In sharp contrast, all of the $plg^{-/-}$ mice had S. aureus in the injected knee joints throughout the entire experimental period (Table 1). At day 28, the amount of S. aureus in the inoculated joints of $plg^{-/-}$ mice was 27-fold higher than the amount injected at day 0. These data show that clearance of bacteria in the knee joints of $plg^{-/-}$ mice were impaired, suggesting that plasmin is involved in the bacterial-killing process during host defense against infection.

TABLE 1

Recovery of bacteria in knee joints of $plg^{+/+}$ and $plg^{-/-}$ mice after intraarticular injection of $1 \times 10^6$ CFU of S. aureus Philips

| Days after bacterial injection | Mean number of bacteria* | | Incidence** | |
|---|---|---|---|---|
| | $Plg^{+/+}$ | $Plg^{-/-}$ | $Plg^{+/+}$ | $Plg^{-/-}$ |
| 2 | $(7.6 \pm 3.7) \times 10^5$ | $(2.9 \pm 1.5) \times 10^6$ | 5/5 | 3/3 |
| 3 | $(3.7 \pm 0.9) \times 10^5$ | $(2.3 \pm 0.5) \times 10^6$ | 5/5 | 5/5 |
| 4 | $(3.0 \pm 0.6) \times 10^5$ | $(1.7 \pm 0.3) \times 10^6$ | 5/5 | 5/5 |
| 5 | $(2.2 \pm 0.5) \times 10^5$ | $(1.2 \pm 0.2) \times 10^6$ | 5/5 | 5/5 |
| 7 | $(8.6 \pm 1.3) \times 10^3$ | $(1.9 \pm 0.3) \times 10^6$ | 7/14 | 11/11 |
| 14 | $(4.0 \pm 2.0) \times 10^2$ | $(3.7 \pm 0.6) \times 10^6$ | 2/10 | 10/10 |
| 28 | undetectable | $(2.7 \pm 0.6) \times 10^7$ | 0/10 | 10/10 |

*Average bacterial counts in knee joints that had detectable levels of living bacteria.
**Data represent the number of knee joints with detectable levels of living bacteria divided by the total number of knee joints examined in each group.

Example 4

Infiltration of the Infected Joints by Macrophages and Neutrophils is not Overtly Impaired in $plg^{-/-}$ Mice Methods This experiment was performed in a similar manner as Example 1, except for the immunohistochemical analysis and inflammatory cell counting.

Immunohistochemical analysis. Paraffin-embedded sections (8-μm) were deparaffinized, rehydrated, and the endogenous peroxidase activity was blocked with 0.3% $H_2O_2$ for 10 min. After incubation with 5% rabbit serum at room temperature for 20 minutes, the slides were incubated at 4° C. overnight with rat anti-mouse primary antibodies against macrophages (clone F4/80, MCAP497, Serotec, UK) or against neutrophils (MCA771G, Serotec, UK), respectively. Thereafter, for macrophage and neutrophil immunostainings, the slices were rinsed and incubated further with goat anti-rat IgG (SC-2019, Santa Cruz, Calif.) antibody at room temperature for 1 hour.

Inflammatory cell counting. The total number of cells per section derived from an area of 5 fields at ×400 magnification. The whole counting procedure was done in duplicates for each section and a mean value per section was calculated. Three independent sections were counted from each joint and five joints from separate mice of the same genotype were used at each time point.

Results

Figure 3:
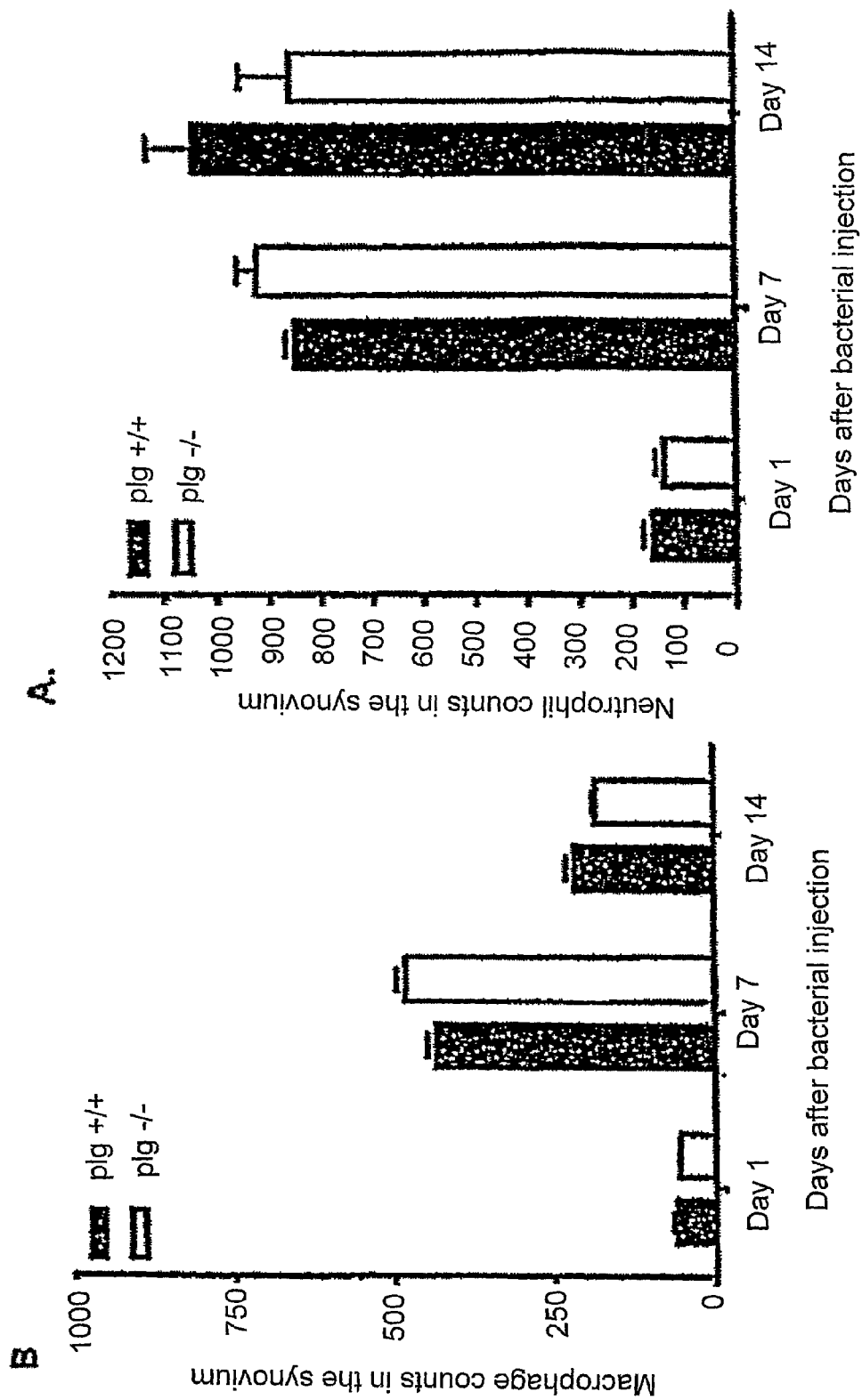
FIG. 3. Neutrophil and macrophage numbers in the infected knee joints of plg$^{+/+}$ and plg$^{-/-}$ mice that were given an intraarticular injection of 1×10$^6$ CFU of S. aureus. A. Infiltrated neutrophil numbers were compared on day 1, day 7 and day 14 after bacterial injection. Bars represent mean value of 5 mice. B. Infiltrated macrophage numbers were compared on day 1, day 7 and day 14 after bacterial injection. Bars represent mean value of 5 mice. Error bars show SDs.

Immunohistochemical analysis was performed to investigate the infiltration of macrophages and neutrophils into the infected knee joints in $plg^{+/+}$ and $plg^{-/-}$ mice. Inflammatory cell infiltration was quantified by counting the number of positively-stained cells presenting on the sections. Three independent sections were counted from each joint and 5 joint samples from each genotype at each time point were included in the study (FIGS. 3A and 3B). In both $plg^{+/+}$ and $plg^{-/-}$ mice, similar numbers of neutrophils and macrophages had infiltrated into the synovium of the infected knee joints within 24 hours of bacterial injection. Thereafter at days 7 and 14, the numbers of accumulated neutrophils and macrophages in both $plg^{+/+}$ and $plg^{-/-}$ mice had increased significantly as compared to that of day 1. These data indicate that, from within 24 hours till day 14 after bacterial injection, neither neutrophil nor macrophage infiltration to the infected joints was impaired in $plg^{-/-}$ mice as compared to $plg^{+/+}$ mice. However, although the infiltration of neutrophils and macrophages was overtly impaired in plg−/− mice, the normal function of these cells, especially the ability to kill bacteria, was severely compromised.

Example 5

Systemic Supplementation of $plg^{-/-}$ Mice with Human Plasminogen (hPlg) Restored the Normal Host Defense Against S. aureus Infection Methods This experiment was performed in a similar manner as Example 1, except for the administration of human plasminogen to some of the mice and western analysis.

Supplementation of $plg^{-/-}$ Mice with Human Plasminogen.

For experimental protocol 1, arthritis was induced by local inoculation of 1×10⁶ CFU of S. aureus Phillips in 10 μl sterile PBS into both knee joints of mice. 6 hours before bacterial inoculation, each of 6 $plg^{-/-}$ mice was supplemented with 1 mg human plasminogen (hPlg) (Biopool, Umeå, Sweden) in 100 μl sterile PBS by intravenous (i.v.) injection at 24-hour intervals for 7 days. As controls, 6 $plg^{+/+}$ and 6 $plg^{-/-}$ mice were injected with sterile PBS alone at 24-hour intervals during 7 days experimental period. Mice were sacrificed at day 7 after bacterial injection and knee joint samples were dissected, decalcified and processed for histological and immunohistochemical analysis.

For experimental protocol 2, arthritis was induced as experimental protocol 1. From day 7 after bacterial inoculation, each of 6 $plg^{-/-}$ mice was supplemented with 1 mg hPlg in 100 μl sterile PBS by i.v. injection. The same amount of plasminogen was injected thereafter at 24-hour intervals for 7 days. As controls, 6 $plg^{+/+}$ and 6 $plg^{-/-}$ mice were injected with sterile PBS alone at 24-hour intervals for 7 days. Mice were sacrificed at day 14 post injection and knee joint samples were dissected, decalcified and processed for histological analysis.

Results

Figure 4:
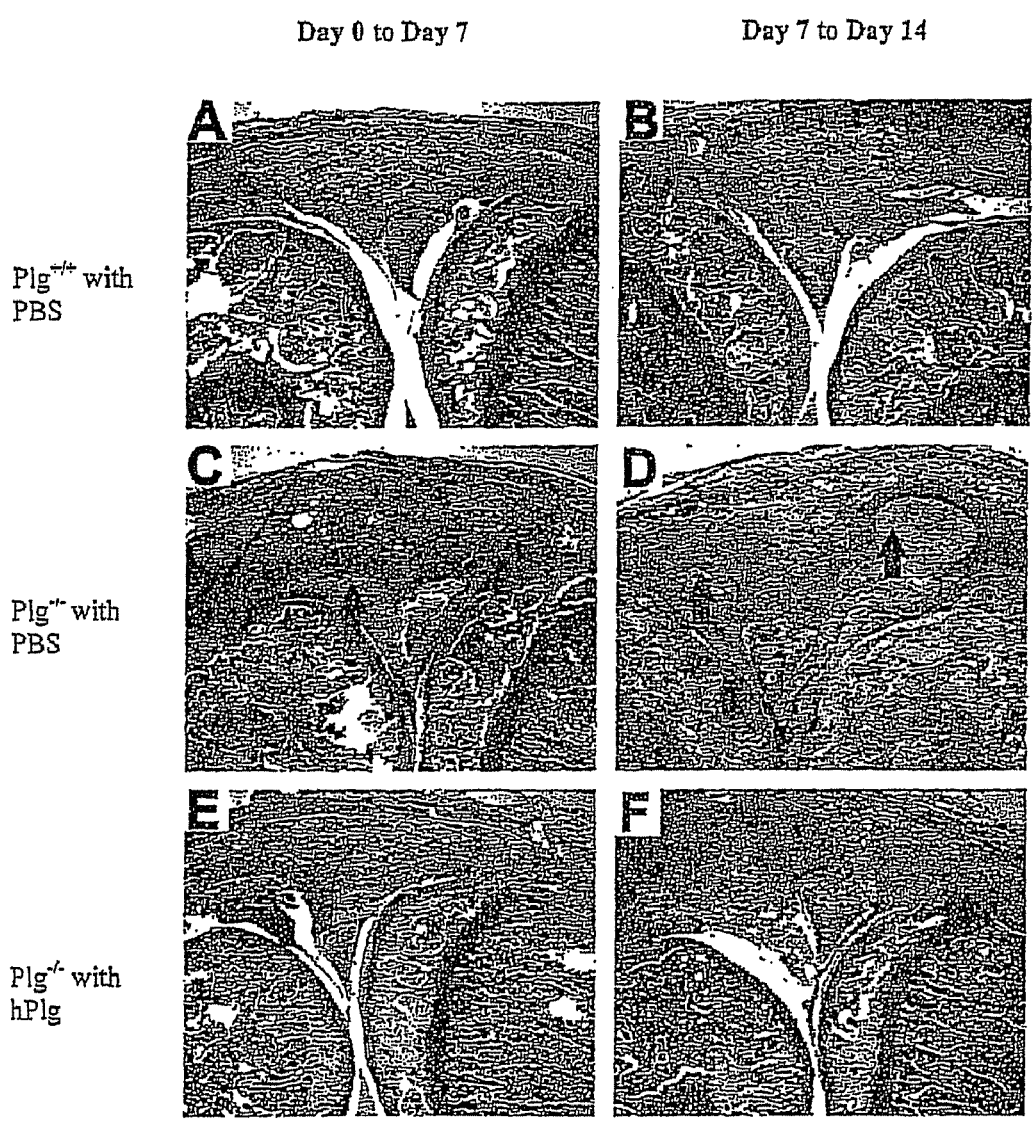
FIG. 4A-F. Histological analysis of whole knee joint from plg$^{+/+}$ and plg$^{-/-}$ mice after plasminogen supplementation. A, B: Control arthritic knee joints from plg$^{+/+}$ mice on days 7 and 14, respectively, after bacterial injection. C, D: Control arthritic knee joints (injected with PBS) from plg$^{-/-}$ mice on days 7 and 14, respectively, after bacterial injection. E: Plg$^{-/-}$ arthritic knee joints supplemented with human plasminogen (hPlg) from day 0 to day 7 after bacterial injection. F: Plg$^{-/-}$ arthritic knee joints supplemented with human plasminogen from day 7 to day 14 after bacterial injection.

To confirm that plasmin plays a role in host defense against *S. aureus*-induced bacterial arthritis, we investigated the development of bacterial arthritis in plg$^{-/-}$ mice supplemented with hPlg. We first performed an experiment where 6 plg$^{-/-}$ mice were supplemented with hPlg from day 0 to day 7 after bacterial injection. We then investigated the effects of supplementation of hPlg on 6 plg$^{-/-}$ mice that had already developed bacterial arthritis for 7 days. As shown in FIGS. 4A and 4B, when plg$^{+/+}$ mice received sterile PBS, moderate levels of inflammation were observed in the synovium and the bone structure was relatively intact. As shown in FIGS. 4C and 4D, when plg$^{-/-}$ mice received only sterile PBS, necrotic tissue was observed in parts of the synovial tissues, the inflammation and tissue destruction were much more severe than in the plg$^{+/+}$ group. When plg$^{-/-}$ mice were supplemented with hPlg from day 0 to day 7 (FIG. 4E), the histopathological features resembled that in plg$^{+/+}$ mice receiving PBS. As shown in FIG. 4F, when plg$^{-/-}$ mice were given hPlg from day 7 to day 14, the joint morphology was substantially more intact than that in plg$^{-/-}$ mice receiving PBS, and the levels of inflammation were comparable to the plg$^{+/+}$ control group. In addition, there was very small area necrotic tissue in the synovium in the group receiving hPlg. As shown in Table 2, the ability to kill bacteria was also restored when plg$^{-/-}$ mice were supplemented with hPlg for 7 days after bacterial injection. These data clearly show that plasmin(ogen) is essentially required for the clearance of *S. aureus* in arthritic knee joints and for the integrity of host defense against infection.

6 plg$^{-/-}$ mice were locally injected around the knee joint tissue with 40 ul of sterile PBS alone at 15 minutes after bacterial inoculation, and thereafter at 24-hour intervals during 7 days experimental period. As controls for wild-type mice, 2 plg+/+ mice were given 40 ul of sterile PBS alone at 15 minutes after bacterial inoculation, and thereafter every 24 hours for 7 days. As controls for plg-/- mice with systemic injections, 2 plg-/- mice were given 100 μl human plasminogen (10 μg/μl) intravenously 1 hour before bacterial inoculation and thereafter every 24 hours for 7 days.

Mice were sacrificed at day 7 after bacterial inoculation and the knee joints were taken and homogenized in 1 ml sterile PBS. After serial dilutions, the solutions of homogenates were spreaded on LB agar plates and incubated at 37° C. overnight. Viable bacterial colonies were then counted to evaluate the number of *S. aureus* bacteria in each homogenate.

Figure 9:
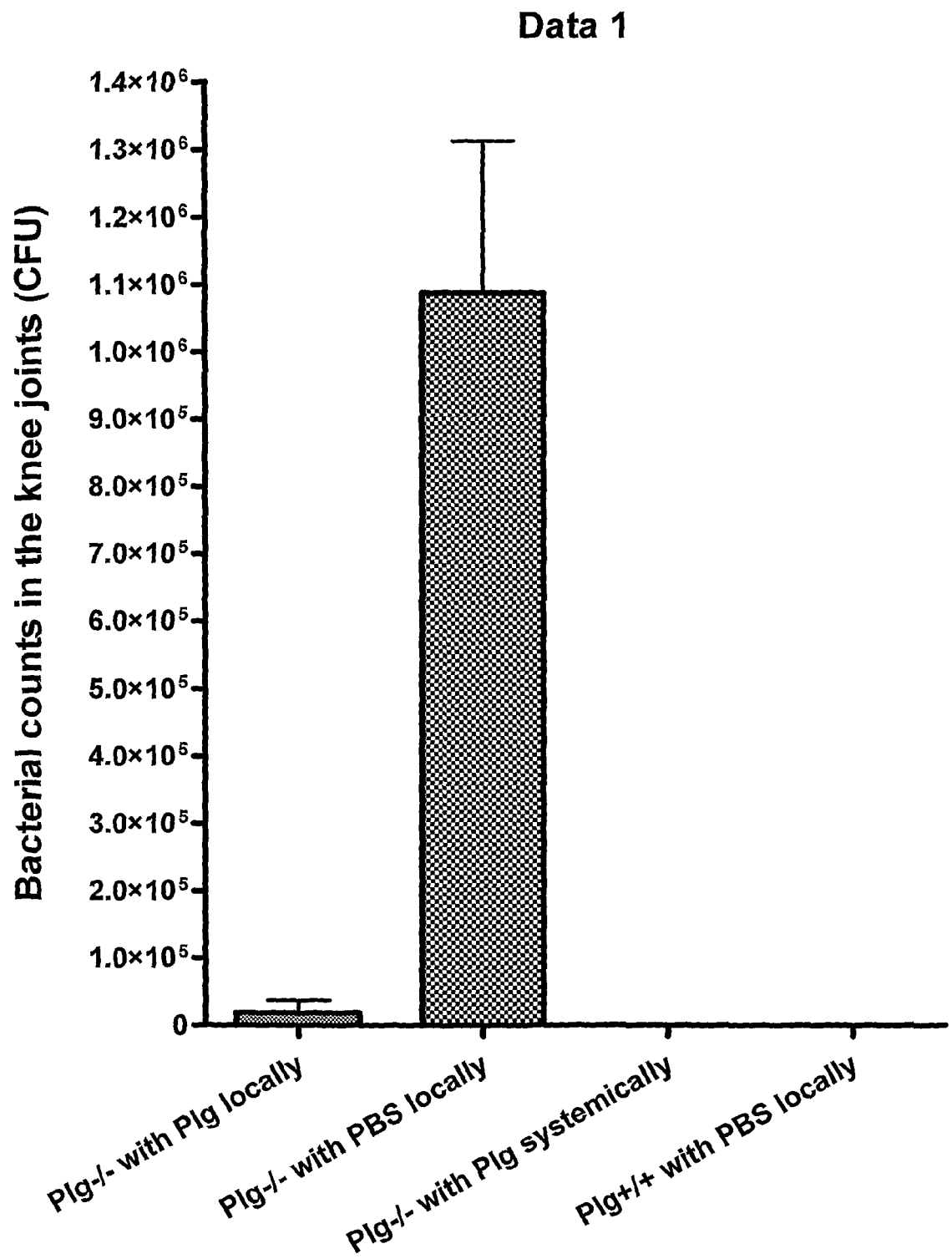
FIG. 9. Bacterial numbers in knee joints of plg−/− and plg+/+ mice with different local and systemic treatments after inoculation of 1×10$^6$ CFU of S. aureus Phillips at the knee joints.

Results 7 days of local injection of plasminogen to plg-/- mice inoculated with *S. aureus* successfully and significantly decreased the amounts of bacteria to 100-folds as compared to the PBS local treatment in these mice (Table 3 and FIG. 9). Both plg-/- mice with systemic injection of human plasminogen or plg+/+ mice with local injection of PBS have also successfully killed *S. aureus* in their knee joints. These data clearly demonstrate that local injection of human plasminogen can restore the normal bacterial killing capacity in the plg-/- mice.

TABLE 2

Recovery of bacteria in the infected knee joints after supplementation of plg$^{-/-}$ mice with plasminogen

| | Mean bacterial counts in the joints* (CFU) | | |
|---|---|---|---|
| | Plg$^{+/+}$ mice given PBS | Plg$^{-/-}$ mice given PBS | Plg$^{-/-}$ mice given human plasminogen |
| Days 0-7 | $(3.2 \pm 2.0) \times 10^3$, n = 6 | $(1.3 \pm 0.12) \times 10^6$, n = 6 | $(1.3 \pm 0.43) \times 10^{3**}$, n = 6 |
| Days 7-14 | $(7.2 \pm 4.3) \times 10^2$, n = 6 | $(2.2 \pm 0.59) \times 10^6$, n = 6 | $(1.8 \pm 0.56) \times 10^{3**}$, n = 6 |

*Average bacterial counts in knee joints that had detectable amounts of living bacteria.
**P < 0.01. The group of plg$^{-/-}$ mice given human plasminogen was compared with the group of plg$^{-/-}$ mice given PBS.

Example 6

Local Supplementation of plg$^{-/-}$ Mice with Human Plasminogen (hPlg) Restored the Normal Host Defense Against *S. Aureus* Infection Methods Bacterial arthritis was induced by local inoculation of $1 \times 10^6$ CFU of *S. aureus* Phillips in 10 μl sterile PBS into both knee joints of mice. 15 minutes after bacterial inoculation, one side of the knee joints of 6 plg$^{-/-}$ mice was supplemented with 40 μl of human plasminogen (10 μg/μl in PBS, Biopool, Umeå, Sweden) by local injections around the knee joint tissue. Thereafter human plasminogen was supplemented at 24-hour intervals for 7 days. As controls for local injections,

TABLE 3

Bacterial number in plg-/- and plg+/+ mice with different local and systemic treatments at day 3 after inoculation of $1 \times 10^6$ CFU of *S. aureus* Phillips

| Groups | Number of samples | Mean number of bacteria (Mean ± SD, × $10^6$ CFU) |
|---|---|---|
| Plg-/- with local injection of hPlg | 6 | 0.019 ± 0.044* |
| Plg-/- with local injection of PBS | 6 | 1.09 ± 0.55 |
| Plg-/- with systemic injection of hPlg | 2 | 0.00075 ± 0.0011* |
| Plg+/+ with local injection of PBS | 2 | 0.00065 ± 0.00092* |

*P < 0.05, compared to the group of plg-/- mice with local injection of PBS.

Example 7

Local Supplementation of plg$^{+/+}$ Mice with Human Plasminogen Enhances the Host Defense Against *S. aureus* Infection Methods Bacterial arthritis was induced by local inoculation of 1×10$^6$ CFU of *S. aureus* Phillips in 10 µl sterile PBS into knee joints of mice. 15 minutes after bacterial inoculation, one side of the knee joints of 7 plg$^{+/+}$ mice was supplemented with 50 µl of human plasminogen (hPlg, 10 µl in PBS, Biopool, Umeå, Sweden) by local injections under the knee skin and around the knee joint tissue. Thereafter human plasminogen was supplemented in the same pattern at 24-hour intervals from day 0 to day 2. As controls for local injections, 7 plg$^{+/+}$ mice were locally injected under the knee skin and around the knee joint tissue with 50 ul of sterile PBS alone at 15 minutes after bacterial inoculation, and thereafter the same local injections were performed at 24-hour intervals from day 0 to day 2 of the experimental period.

Mice were sacrificed at day 3 after bacterial inoculation and the knee joints were taken and homogenized in 1 ml sterile PBS. After serial dilutions, the solutions of homogenates were spread on LB agar plates and incubated at 37° C. overnight. Viable bacterial colonies were then counted to evaluate the number of *S. aureus* bacteria in each homogenate.

Results

Figure 10:
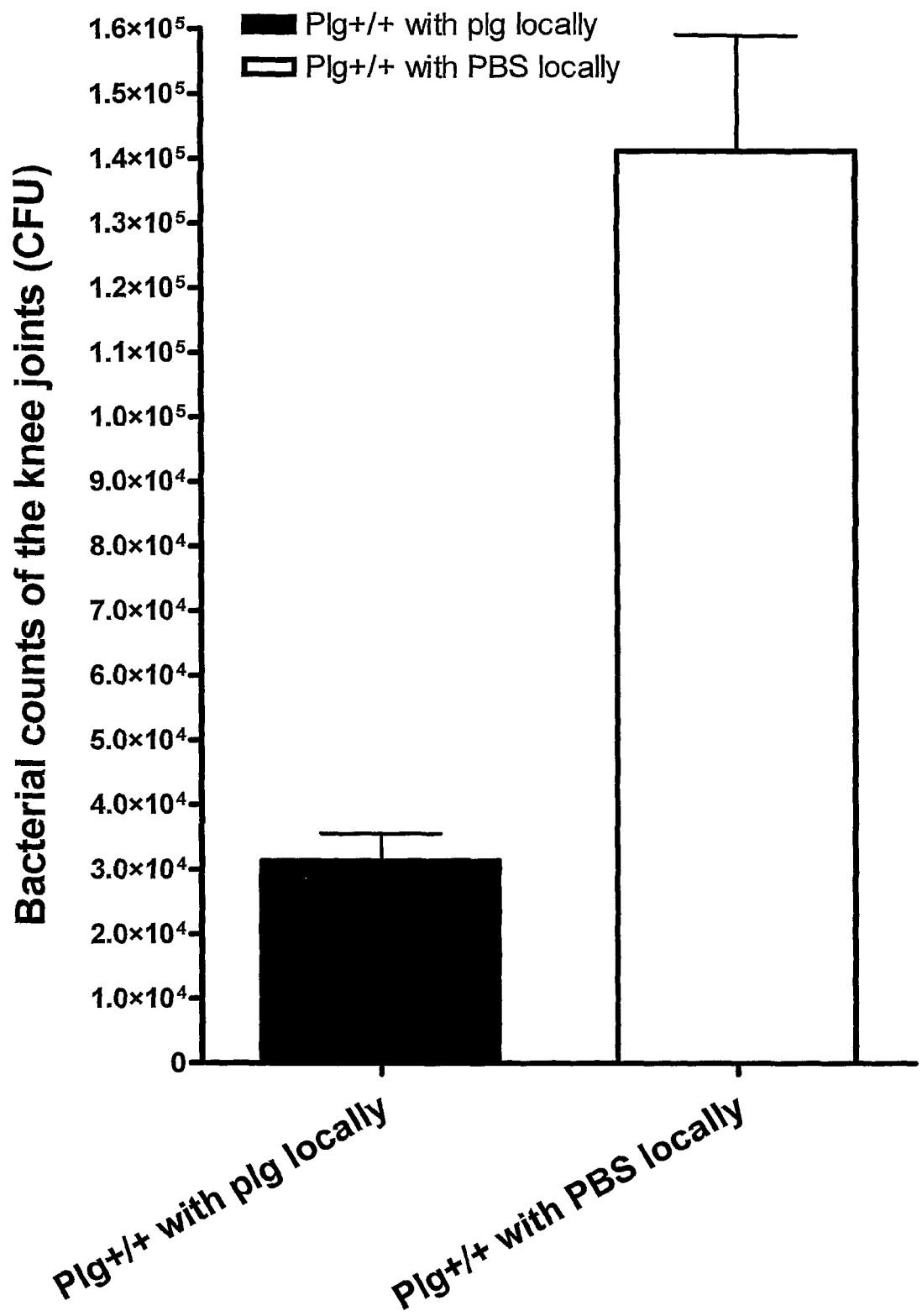
FIG. 10. Bacterial numbers in knee joints of plg+/+ mice after local injection with Plg (closed box) or PBS (open box) 3 days after inoculation of S. aureus at the knee joints. Note in wild-type mice locally injected with Plg the bacterial number is significantly lowered for 5 folds than that of wild-type locally injected with PBS.

Local injection at the knee joints of human plasminogen for 3 days in plg+/+ mice successfully and significantly reduced the living *S. aureus* number for 5 folds as the control plg+/+ group treated PBS. These data clearly demonstrate that human plasminogen is a potent pro-inflammatory factor that potentiates the host defense against bacterial infection even in wild-type animal. These data (Table 4, FIG. 10) further indicate that plasminogen is a novel anti-infectious drug candidate for clinical use.

TABLE 4

Bacterial number in wild-type (plg+/+) mice locally injected with human plasminogen or PBS at day 3 after inoculation of 1 × 10$^6$ CFU of *S. aureus* Phillips

| Groups | Number of samples | Mean number of bacteria (Mean ± SE, × 10$^6$ CFU) |
|---|---|---|
| Plg+/+ with local injection of hPlg | 7 | 0.031 ± 0.011* |
| Plg+/+ with local injection of PBS | 7 | 0.14 ± 0.047 |

*P < 0.05, as compared to the group of Plg+/+ mice with local injection of PBS.

Example 8

Supplementation of plg$^{-/-}$ Mice with Plasminogen Increased the IL-6 Protein Expression in the Infected Knee Joints Methods This experiment was performed in a similar manner as Example 5, except for the immunohistochemical staining of IL-6.

For IL-6 immunostaining, the slices were rinsed and incubated with Swine anti-rabbit IgG antibody (P0217, DAKO, Denmark) at room temperature for 1 hour. The chromogenic reaction was developed by DAKO substrate kit (K3464, DakoCytomation AEC substrate, USA) and the slides were counterstained with hematoxylin. Slides incubated with rabbit serum instead of the primary antibody served as negative control, they all showed negative.

Results

Figure 5:
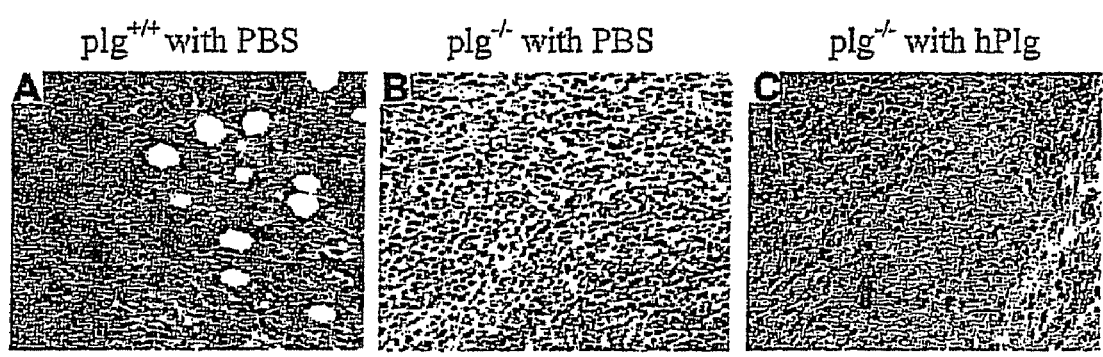
FIG. 5A-C. IL-6 protein expression levels in the synovium. Immunostaining of representative sections of knee joints from plg$^{+/+}$ and plg$^{-/-}$ mice. A: Control arthritic knee joints treated with PBS from plg$^{+/+}$ mice on day 7 after bacterial injection. B: Control arthritic knee joints treated with PBS from plg$^{-/-}$ mice on day 7 after bacterial injection. C: Plg$^{-/-}$ arthritic knee joints supplemented with human plasminogen (hPlg) from day 0 to day 7 after bacterial injection. Pink color shows the IL-6 in the synovium (arrow).

IL-6 has been reported to be involved in lymphocyte activation, growth and differentiation and lack of IL-6 enhances the susceptibility to infection. We therefore investigated whether plasmin has any effect on IL-6 expression during bacterial arthritis. Samples for tissue section were taken during supplementation of plg$^{-/-}$ mice with hPlg and performed by immunohistochemical stainings When plg$^{-/-}$ mice received sterile PBS for 7 days after bacterial injection, the IL-6 protein levels were significantly lower as compared to plg$^{+/+}$ mice (FIGS. 5A and 5B). As shown in FIG. 5C, when plg$^{-/-}$ mice received hPlg for 7 days after bacterial injection, the IL-6 protein expression was increased to a similar level as the plg$^{+/+}$ mice. These data show that plasmin is involved in the regulation of IL-6 expression in knee joints during bacterial arthritis.

Example 9

Higher Levels of IL-10 Expression in plg$^{+/+}$ Joints as Compared to plg$^{-/-}$ Joints Methods This experiment was performed in a similar manner as Example 1, except for the western blots analysis.

Western Blots Analysis.

At days 3 and 7 after bacterial injection, mice were sacrificed and the whole knee joints were collected. Joints were homogenized and lysed in NP-40 buffer (0.5% Nonidet P-40, 50 mM Tris-HCl (pH 7.4), 150 mM NaCl, 1 mM NaF, 1 mM EDTA, 1 mM Na$_3$VO$_4$, 0.25 mM PMSF, 5 µg/ml aprotinin, 1 µg/ml leupeptin, 1 µg/ml pepstatin, and 15% glycerol) for 30 min on ice. The lysates were adjusted for equal protein concentration. The western blot analysis were performed as described (12), using a goat-anti-mouse IL-10 antibody (AF-417-NA, R & D systems, UK) and mouse monoclonal antibody against β-actin (Sigma-Aldrich Sweden AB, Stockholm, Sweden). Anti-goat and anti-mouse secondary antibodies conjugated with horseradish peroxidase (HRP) were from Biorad (Hecules, Calif., USA).

Results

Figure 6:
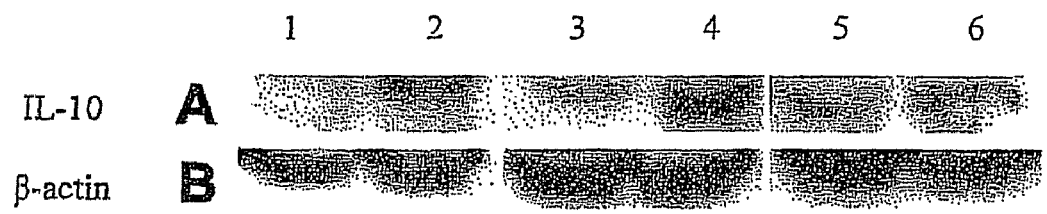
FIG. 6A-B. Western blot analysis of the expression level of IL-10 protein in uninfected and infected knee joints. A, levels of IL-10 in the lysates. Lane 1: uninfected knee joint lysates of plg$^{-/-}$ mice; Lane 2 uninfected knee joint lysates of plg$^{+/+}$ mice; Lane 3: plg$^{-/-}$ arthritic knee joints lysates at day 3 after bacterial injection; Lane 4: plg$^{+/+}$ arthritic knee joints lysates at day 3 after bacterial injection; Lane 5: plg$^{-/-}$ arthritic knee joints lysates at day 7 after bacterial injection; Lane 6: plg$^{+/+}$ arthritic knee joints lysates at day 7 after bacterial injection. B, Levels of β-actin in the lysates correspondent to each lane in A as control. Experiments were repeated at least 3 times and representative results were shown.

Previous studies have demonstrate that interleukin-10 (IL-10) have anti-inflammatory effects in animal model of septic arthritis (13). To study whether plasmin has any effects on IL-10 expression during bacterial arthritis, western blot analysis was performed to compare the IL-10 levels between plg$^{+/+}$ and plg$^{-/-}$ mice. At days 3 and 7 after bacterial injection, joint homogenates were lysed and performed with western blotting for IL-10. Plg$^{-/-}$ mice have dramatically lower IL-10 levels compared with plg$^{+/+}$ mice in un-infected knee joints. (FIG. 6A, lanes 1 and 2, respectively). At day 3, the IL-10 levels in both genotype mice were elevated, although plg$^{-/-}$ still have markedly lower levels of IL-10 as compared to plg$^{+/+}$ mice. (FIG. 6A, lanes 3 and 4). At day 7, plg$^{-/-}$ mice still have same levels of IL-10 as compared to day 3, whereas the IL-10 levels were decreased in plg$^{+/+}$ mice (FIG. 6A, lane 5, lane 6). Taken together these data suggest that IL-10 in concert with IL-6 may regulate inflammatory process during bacterial arthritis and plasmin is involved in the regulation of IL-6 and IL-10 expression.

Example 10 uPA is Important for Host Defense and Tissue Remodeling Against *S. Aureus* Induced Knee Infection Methods At day 0, bacterial arthritis was induced by local intra-articular inoculation of 1×10$^6$ CFU of *S. aureus* Phillips in 10

μl sterile PBS into knee joints of wild-type and uPA-deficient (uPA−/−) mice (14). Mice were sacrificed on days 7, 14, 21 and 28, and the knee joints were taken and homogenized in 1 ml sterile PBS. After serial dilutions, the solutions of homogenates were spread on LB agar plates and incubated at 37° C. overnight. Viable bacterial colonies were then counted to evaluate the number of S. aureus bacteria in each homogenate.

In another experiment, uPA-deficient and wild-type mice were induced with bacterial arthritis by local intra-articular inoculation of $1\times10^6$ CFU of S. aureus Phillips in 10 μl sterile PBS into knee joints. At days 7, 14, and 28 after bacterial injection, mice were sacrificed and samples of whole knee joints were collected for histological analysis. In brief, knee joints were first fixed in 4% paraformaldehyde, embedded in paraffin, and thereafter 8-μm sections were prepared. Slides containing tissue sections were stained with Safranin-O for histological analysis. At least 10 knee joints were included in each experimental group.

Results

Figure 11:
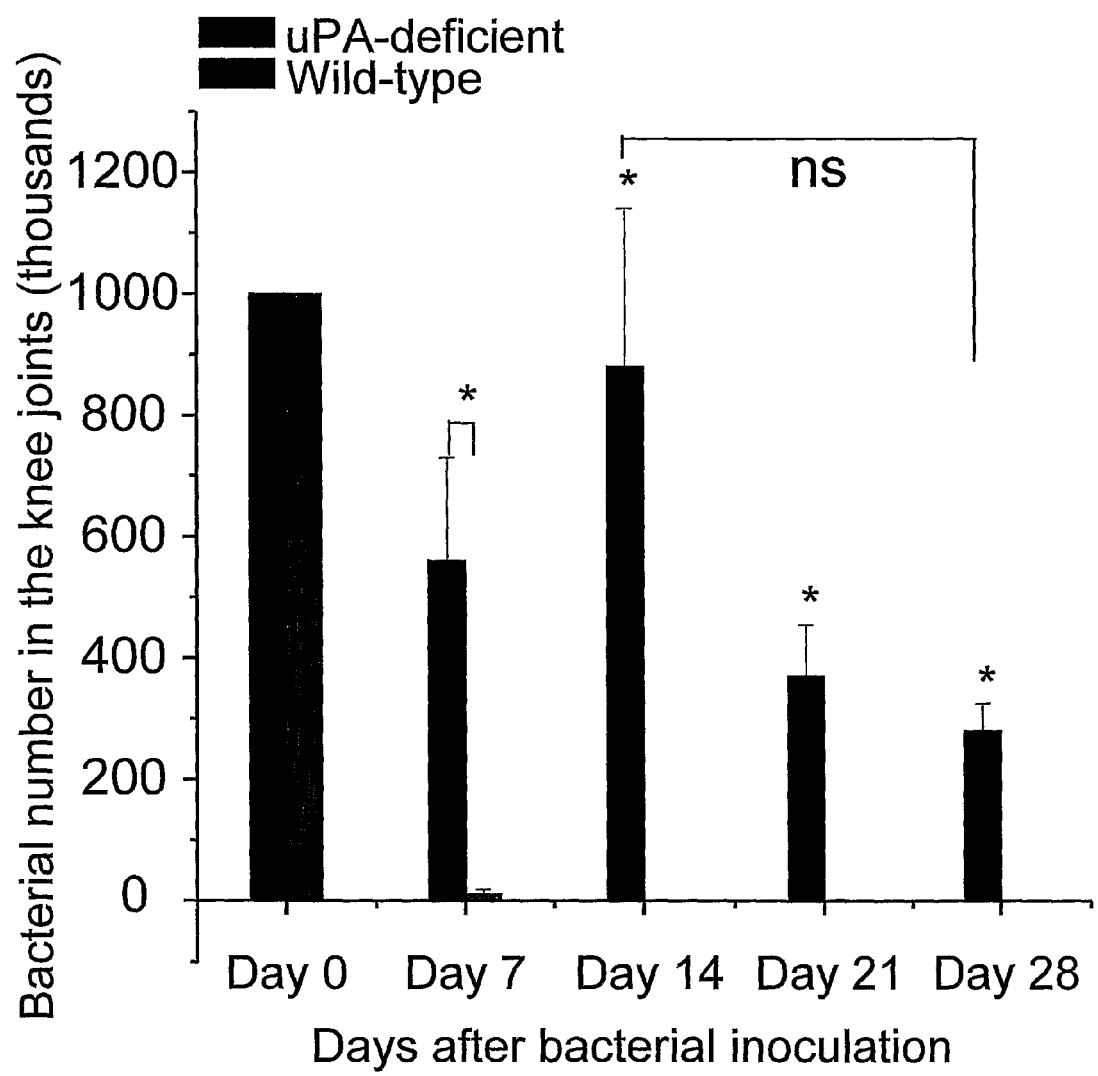
FIG. 11. Bacterial numbers in knee joints of uPA-deficient and wild-type mice. Note in wild-type mice the bacterial number quickly subsided after the inoculation of S. aureus at day 0, whereas in uPA-deficient mice the number of bacteria were constantly over $2.0 \times 10^5$ CFU throughout the experimental period.
Figure 12:
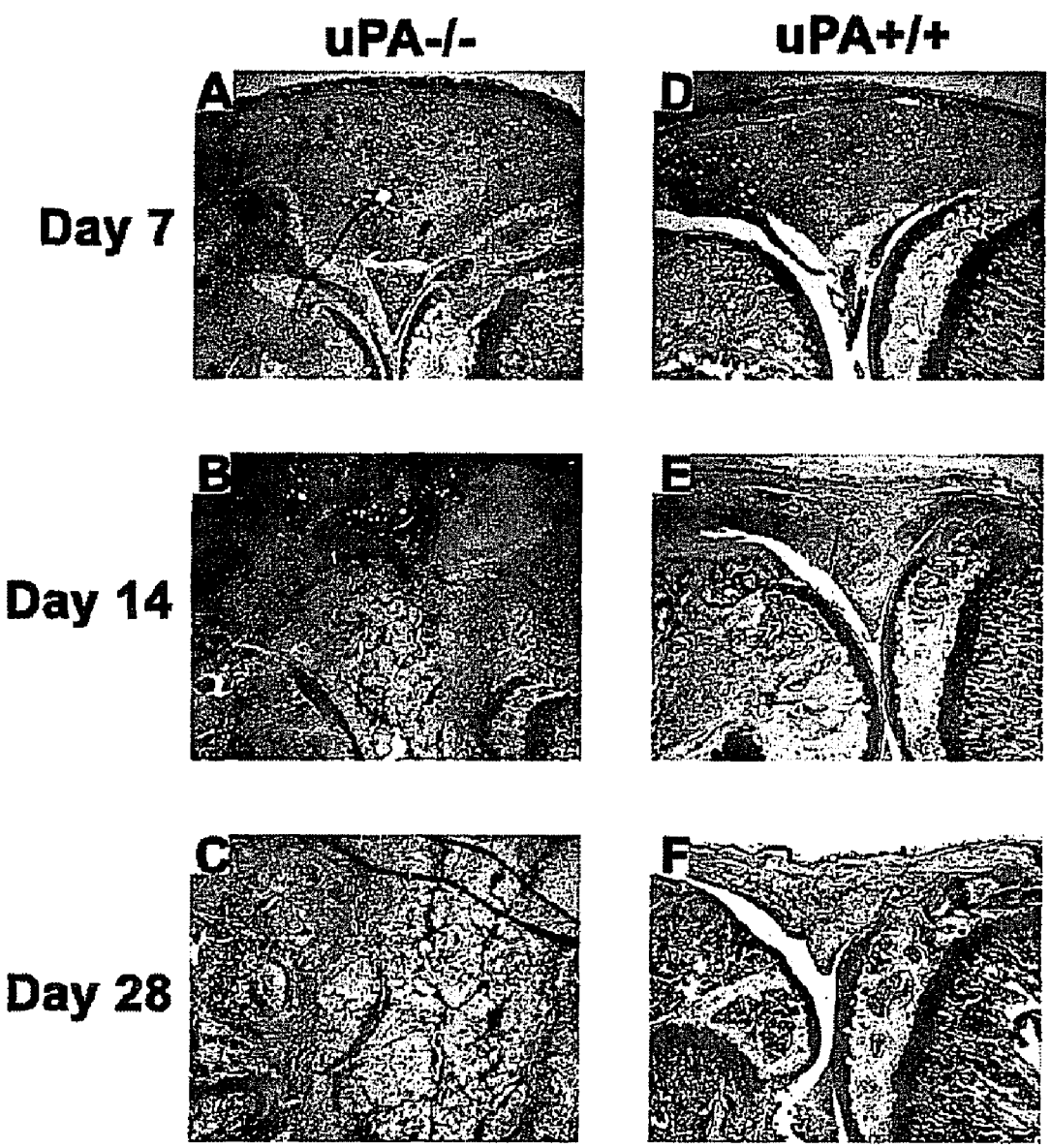
FIG. 12A-F. Histologies of representative sections of arthritic knee joints from uPA-deficient (uPA$^{-/-}$, left) and wild-type (uPA$^{+/+}$, right) mice at days 7 (A, D), 14 (B, E) and 28 (C, F) after an intraarticular injection of $1 \times 10^6$ CFU S. aureus. Note in uPA−/− mice there are much more edema, tissue destruction and necrotic tissue formation throughout the experiment, whereas in uPA+/+ mice the inflammation was just transiently present at day 7 after arthritis induction and subsided thereafter.

After induction of S. aureus-induced bacterial arthritis in wild-type and uPA-deficient mice. In the wild-type group, the mean bacterial number is continuously decreasing from day 7 to day 28. At day 14, 4 out of 7 mice have cleaned bacteria completely. However, in uPA-deficient group, the mean bacterial number is basically constant from day 0 to day 28 (FIG. 11). Although bacterial number were decreasing after day 14, there was no significant different between day 14 and day 28. Although the experiment was terminated at day 28 after bacterial inoculation, it is highly unlikely that uPA-deficient mice are able to kill the bacteria at later time points because the knee joint has totally demolished after day 14. From day 14 and on extensive levels of necrotic tissue are accumulated in the uPA-deficient knee joints. For histological examinations, whereas wild-type mice showed transient inflammation at day 7 and the levels of inflammation quickly subsided thereafter, uPA-deficient mice showed persistent tissue inflammation and edema, extensive tissue destruction and formation of necrotic tissue throughout the experimental period (FIG. 12). These data (Table 5, FIGS. 11 and 12) clearly demonstrate that uPA is important in bacterial killing during the host defense against S. aureus-induced arthritis, and further implicate that the components of the plasminogen activator pathway plays critical roles during host defense against infection.

Example 11

Higher Levels of Bodyweight Loss and Severity of Arthritis in Bacterial Arthritis of plg−/− Mice after Intravenous Injection of $1\times10^6$ CFU of S. aureus Phillips in 200 μl Sterile PBS Methods Bacterial arthritis was induced in plg+/+ and plg−/− mice by intravenous (i.v.) injection of $1\times10^6$ CFU of S. aureus Phillips in 200 μl sterile PBS. Mice were followed up individually every day after inoculation. Paws were inspected every 24 hours, and all mice were sacrificed at day 21 after inoculation. Arthritis was defined as visible joint swelling and/or erythema of palm, wrist and ankle. To evaluate the intensity of arthritis, a clinical scoring (arthritic index) was carried out, using a system where macroscopic inspection yielded a score of 0-5 points for each paw. (0=normal, 1=marginal swelling or erythema; 2=mild swelling and erythema; 3=moderate swelling and erythema; 4=marked swelling and erythema; 5=marked swelling and deformity). The total score was calculated by adding the scores from all 4 paws for each animal tested, resulting in an arthritic score ranging from 0 to 20 for each individual mouse. The weight of the mice was determined each day from day 0 to day 21.

Results

To evaluate whether plasminogen deficiency affects the bacterial invasion to the joints in the intravenous injection induced bacterial arthritis model, the onset day and incidence of arthritis, defined as marginal swelling and erythema, were followed (Table 6) every 24 hours after bacterial inoculation. The onset day in $plg^{+/+}$ and $plg^{-/-}$ mice was 5.0±2.2 and 4.4±2.0 respectively (P=0.5021). Furthermore, the incidence of arthritis between $plg^{+/+}$ and $plg^{-/-}$ mice were identical. These results indicate that both $plg^{+/+}$ and $plg^{-/-}$ mice are susceptible to S. aureus induced arthritis by intravenous inoculation. However, a striking observation was noticed in this study, 38% (12/32) of the $plg^{-/-}$ mice were paralysed in the hind part, whereas only 3.3% (1/30) of $plg^{+/+}$ mice showed paralysis.

Figure 13:
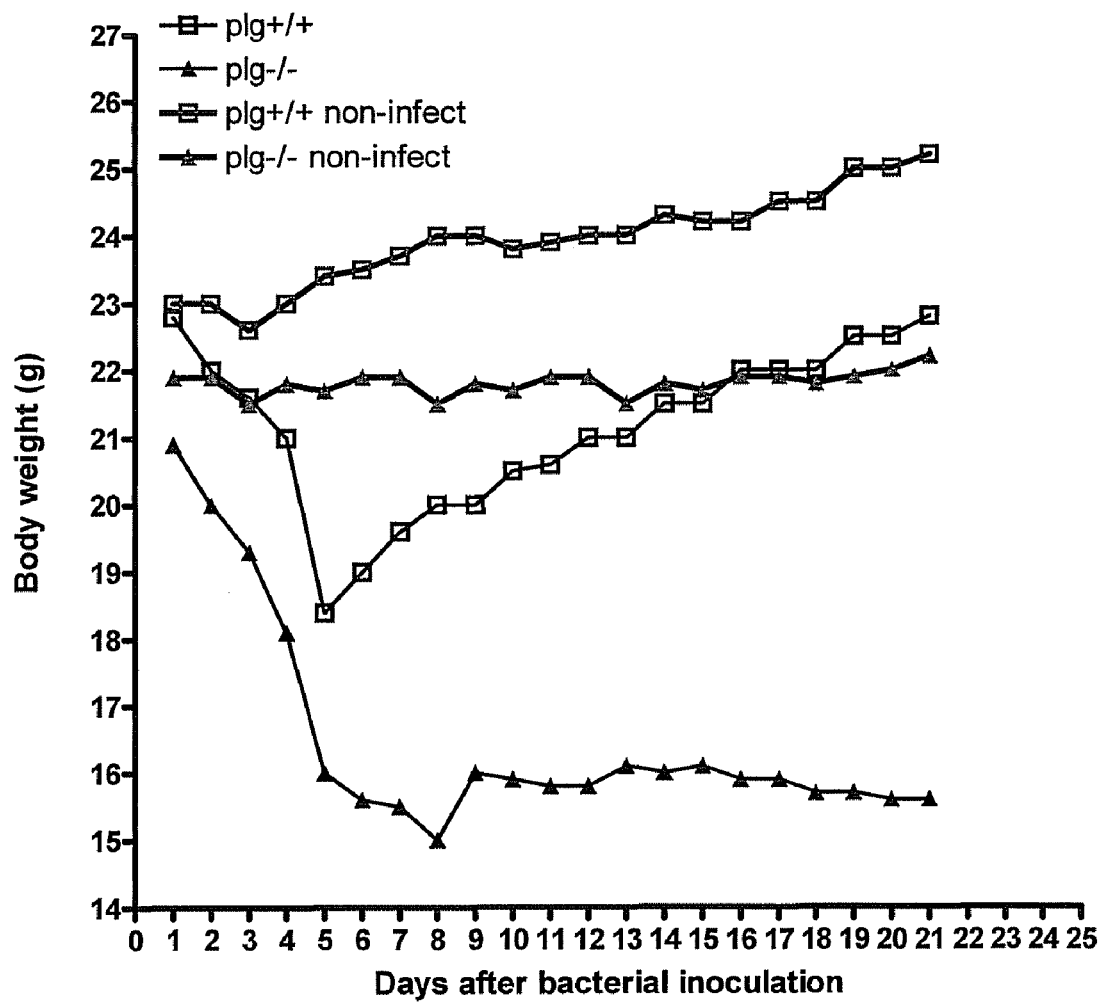
FIG. 13: Comparison of body weight changes between plg$^{+/+}$ and plg$^{-/-}$ mice. Time course of body weight changes after $1 \times 10^6$ CFU of bacterial injection. Mice body weight was checked every 24 hr, from day 1 to day 21.

In order to follow the general health situation after intravenous inoculation of S. aureus, the weight of each mouse was measured every day during the experimental period. As shown in FIG. 13, during the first week of infection, both $plg^{+/+}$ and $plg^{-/-}$ mice showed a substantial weight loss, which reached the maximum 24% and 26% of body weight at day 7, respectively. 7 days after infection, the body weight of $plg^{+/+}$ mice had gradually increased. In contrast, significant

TABLE 5

Incidence and bacterial number in uPA-deficient and wild-type mice after induction of S. aureus-induced bacterial arthritis.

| | uPA-deficient | | Wild-type | | |
| --- | --- | --- | --- | --- | --- |
| Days | Bacterial number (CFU) | Incidence* | Bacterial number (CFU) | Incidence* | P value** |
| Day 0 | $1.0 \times 10^6$ | 2/3 | $1.0 \times 10^6$ | 2/3 | |
| Day 7 | $5.6 \times 10^5 \pm 1.7 \times 10^5$ | 6/6 | $1.1 \times 10^4 \pm 7.9 \times 10^3$ | 6/6 | 0.0103 |
| Day 14 | $8.8 \times 10^5 \pm 2.6 \times 10^5$ | 7/7 | $7.5 \times 10^2 \pm 4.2 \times 10^2$ | 3/7 | 0.006 |
| Day 21 | $3.7 \times 10^5 \pm 8.4 \times 10^4$ | 5/5 | $6.0 \times 10^2 \pm 6.0 \times 10^2$ | 1/5 | 0.0023 |
| Day 28 | $2.8 \times 10^5 \pm 4.5 \times 10^4$ | 5/5 | $6.0 \times 10^2 \pm 6.0 \times 10^2$ | 1/5 | 0.0003 |

*incidence is defined as the proportion of the number of infected knee joints to the number of total knee joints examined at that time point.
**P value is calculated by the comparison of bacterial numbers of all the knee joints between uPA-deficient and wild-type mice at respective time point.

weight loss was continuously observed in plg$^{-/-}$ mice throughout the experiment (p<0.05).

Figure 14:
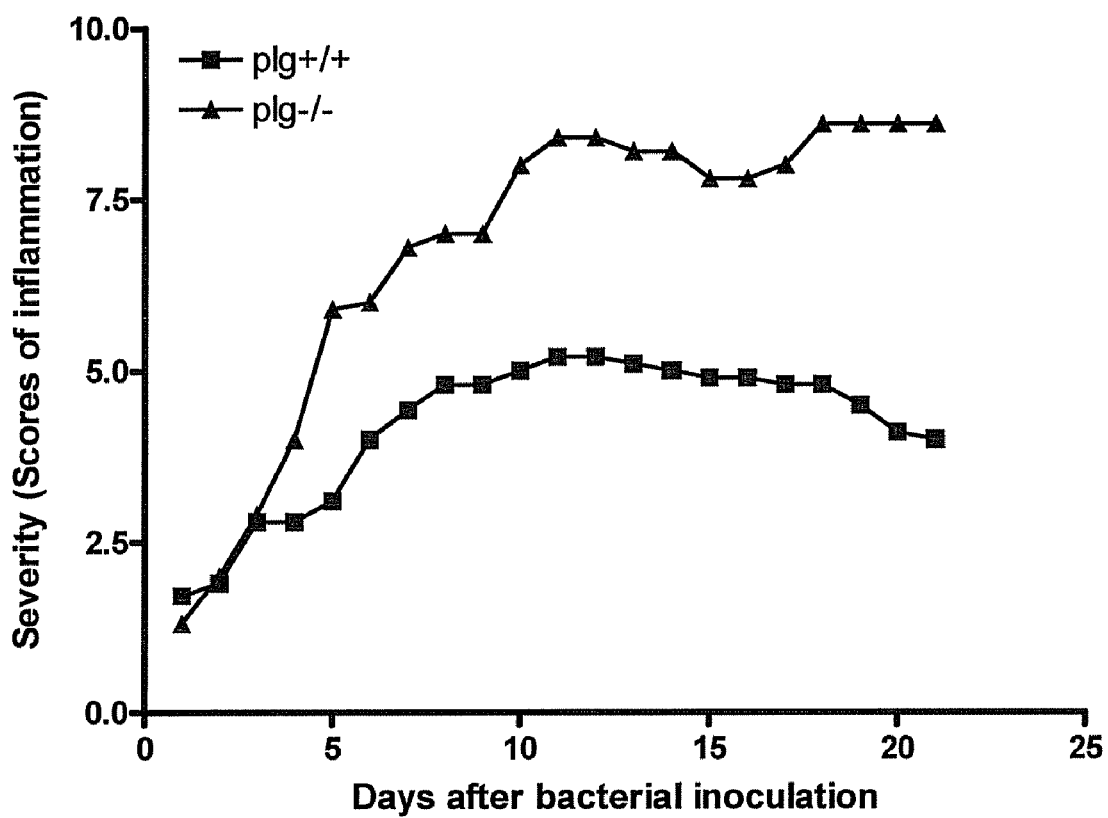
FIG. 14.: Severity of septic arthritis. Results from the evaluation of severity in septic arthritis using arthritic index as described in materials and methods. Arthritis was induced by $1 \times 10^6$ CFU S. aureus Phillips injected intravenously. Plg$^{+/+}$ mice (n=15) and plg$^{-/-}$ mice (n=16). For each time point, mean±SEM are shown. Statistical significance test was performed by using the Mann-whitney u-test (deficient mice versus control mice). * $P<0.05$ was considered significant.

The clinical development of bacterial arthritis was also followed for 3 weeks in plg$^{+/+}$ and plg$^{-/-}$ mice after inoculated i.v. with 1×10$^6$ S. aureus. As shown in FIG. 14, both plg$^{+/+}$ and plg$^{-/-}$ mice developed bacterial arthritis. There was no difference in the severity of inflammation during the first 3 days between plg$^{+/+}$ and plg$^{-/-}$ mice. However, from day 7 and on, the plg$^{-/-}$ mice had more severe inflammation than plg$^{+/+}$ mice, and the difference was significant. (p<0.05). In plg$^{+/+}$ mice, the severity reached peak at day 14 and gradually subsided thereafter. At the end of the experiment, 8 out of 28 plg$^{+/+}$ mice recovered from the arthritis. In plg$^{-/-}$ mice, the severity of arthritis increased during the whole experiment, and none of the plg$^{-/-}$ mice recovered from the arthritis at the end of the experiment. Taken together, these data clearly indicate that plasminogen is not essential in the invasion of bacteria from blood circulation, but essential in host defense against bacterial infection in the knee joints and in maintaining the health situation during bacterial arthritis.

TABLE 6

Comparison of the main features bacterial arthritis in plg+/+ and plg-/- mice after intravenous injection of 1 × 10$^6$ CFU of S. aureus Phillips in 200 µl sterile PBS

|  | Plg$^{+/+}$ | Plg$^{-/-}$ |
| --- | --- | --- |
| Onset day (Mean ± SEM) | 5.0 ± 2.2 | 4.4 ± 2.0 |
| Incidence of bacterial arthritis | 93% (28/30) | 93% (30/32) |
| Incidence of paralysis | 3.3% | 37.5% |
| Incidence of necrosis in infected joint | 0 | 100% |
| Body weight at day 21 | 22.8 g | 16.7 g |

Example 12

More Severe Development of Tissue Destruction and Formation of Necrotic Tissue in Bacterial Arthritis of plg-/- Mice after Intravenous Injection of 1×10$^6$ CFU of S. aureus Phillips in Sterile PBS Methods Bacterial arthritis was induced in plg+/+ and plg-/- mice by intravenous (i.v.) injection of 1×10$^6$ CFU of S. aureus Phillips in 200 µl sterile PBS. Mice were followed up individually every day after inoculation.

To perform histopathological examinations of the ankles and paws, ankles and paws were dissected and fixed in 4% buffered formalin for 24 hours. Fixed tissues were decalcified for 3 weeks in 15% EDTA, dehydrated, and embedded in paraffin. 8 µm sections of the wrist-joints were stained with Safranin-O and counterstained with fast green/iron hematoxylin.

For immunohistochemical analysis, Saraffin-embedded sections (8 µm) were deparaffinized and rehydrated in ethanol and distilled water. Endogenous peroxidase activity was blocked with 3% H$_2$O$_2$ for 10 minutes. Then incubate for 20 min at room temperature with 5% rabbit serum for fibrin detection. Slides were then overlaid with Goat anti-mouse fbn/fbg at room temperature for 30 min. After washing, overlaid rabbit IgG anti-goat IgG for 20 min at RT. After washing, overlaid PAP for 20 min at RT. The color was developed by (DAKO Substrate chromogen system AEC) Kit, and after washing counterstained with Mayer's hematoxylin.

Results

Figure 15:
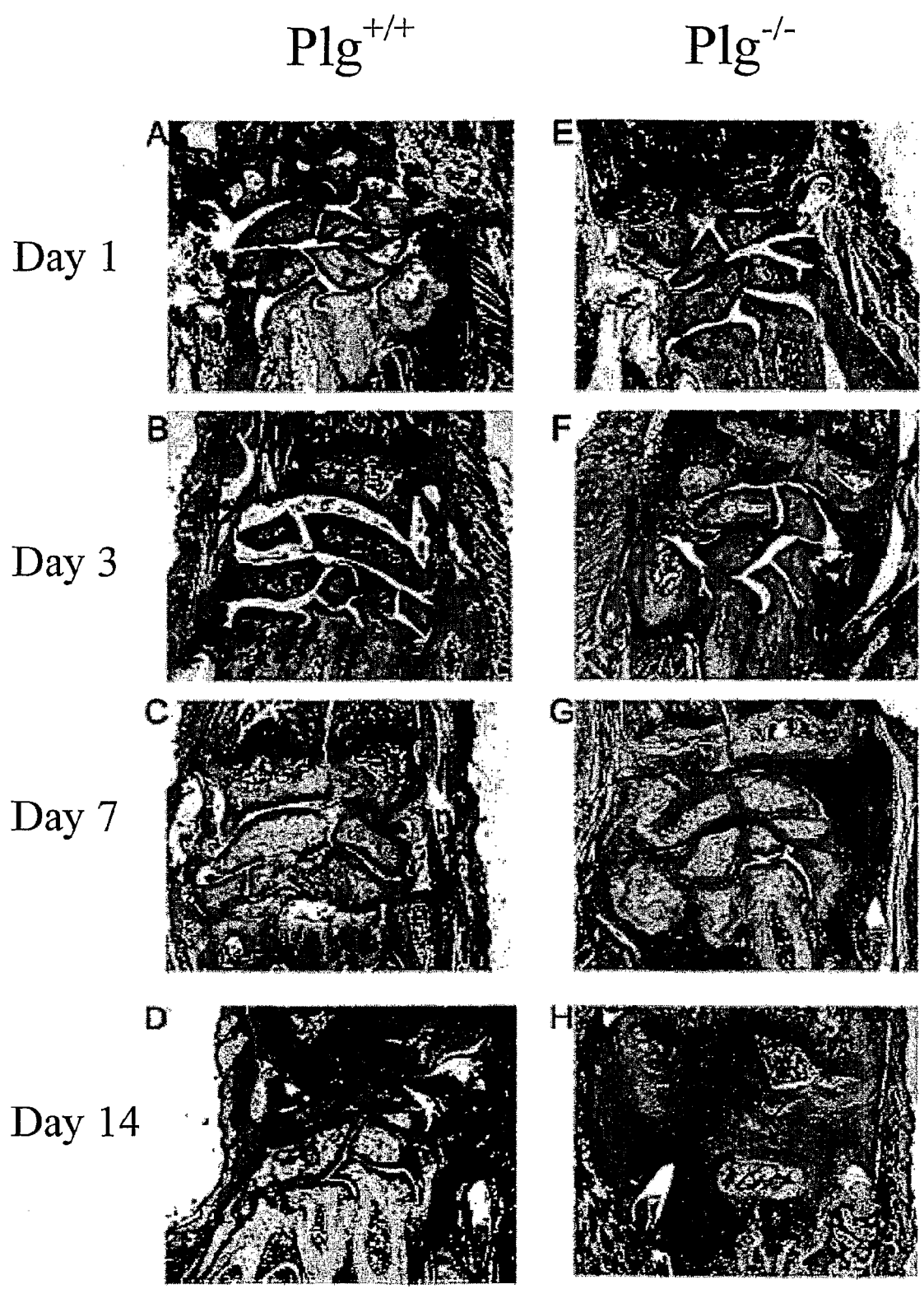
FIG. 15A-H: Plasminogen deficiency exacerbates histological features of septic arthritis. Histologies of paw joints sections stained with Safranin-O. Morphology of the representative sections of arthritic paw joints after intravenous injection of $1 \times 10^6$ CFU S. aureus in plg$^{+/+}$ (left) and plg$^{-/-}$ (right) mice Arthritic paw joints from wild-type mice on days 1 (A), 3 (B), 7 (C) and 14 (D) after arthritis onset. Arthritic paw joints from plg$^{-/-}$ mice on days 1 (E), 3 (F), 7 (G) and 14 (H) after arthritis onset.

To determine whether the observed persistence of joint inflammation was associated with histological changes, paws joints from infected plg$^{+/+}$ and plg$^{-/-}$ mice were performed histological analysis. The joints were stained with safranin-O, and counterstained with fast green/iron and hematoxylin. As shown in FIG. 15, in plg$^{+/+}$ mice, one day after onset day, the inflammation was very slight (FIG. 15A). 3 days after onset day, the synovial membrane becomes hyperplastic but the cartilage was intact (FIG. 15B). 7 days after onset day, inflammatory cells had infiltrated into the joint cavity (FIG. 15C). 14 days after onset day, the synovial membrane was much thicker than that in day 7 (FIG. 15D). In plg$^{-/-}$ mice, as shown in FIG. 15E, one day after onset day, the inflammation level was also slight. However, 3 days after onset day, the synovial membrane was much thicker than that on day 1, and the inflammatory cells started to invade the bone (FIG. 15F). 7 days after onset day, the inflammatory cells filled with the whole paw joint, and some parts of bone had degraded (FIG. 15G). 14 days after onset day, most bones and cartilage was completed degraded (FIG. 15H). In addition, 14 days after onset day, in plg$^{+/+}$ mice, although the inflammation was severe, the severity was very slight compare to plg$^{-/-}$ mice. The clinical findings were verified by the histopathological examination which showed clearly that the plg$^{-/-}$ mice displayed a significantly higher level of both cartilage and bone destruction. Together, the plg$^{+/+}$ mice exhibited a significantly less severe arthritis than plg$^{-/-}$ mice. The plasmin has a beneficial effect on the tissue remodeling.

Figure 16:
FIG. 16A-B: Necrotic tissue in infected ankle joints. Necrosis was base on histological observation. Some samples that were identified as necrosis were further confirmed by TUNEL staining.
Figure 16:

To examine the development and resolution of the arthritis at the cellular level, microscopic analyses for necrotic tissue were performed in plg$^{-/-}$ and plg$^{+/+}$ mice. Necrotic tissue in the joint was found as early as day 3 after bacterial inoculation in plg$^{-/-}$ mice. As shown in FIG. 16 and FIGS. 15G,H, large area of necrotic tissue was found in plg$^{-/-}$ mice, In contrast, little necrosis was found in plg$^{+/+}$ mice, even they have severe inflammation. These data indicate that plg deficient mice unable to remove necrotic tissue and cause tissue destruction.

Figure 17:
FIG. 17A-B: Fibrin deposition in the infected ankle joints. Immunohistochemical detection of fibrin in arthritic knee joints. Paraffin-embedded tissue sections were stained with a rabbit anti-murine fibrin(ogen) antibody. Brown color indicates positivity. Arthritic knee joint on day 14 in plg$^{+/+}$ (left) and plg$^{-/-}$ (right) mice after arthritis onset. Similar fibrin deposition in the plg$^{-/-}$ and plg$^{+/+}$ infected joints.
Figure 17:
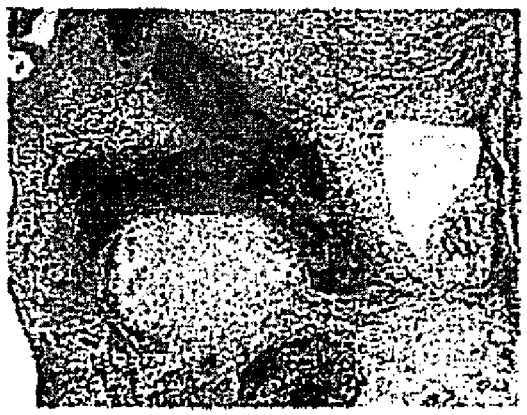

Based on the established role of plasminogen activation in fibrinolysis, loss of plasminogen results in increased fibrin deposition. Fibrin content in knee joints was analyzed by fibrin immunohistochemistry (FIG. 17). However, we found similar levels of fibrin deposition in all swollen joints of the plg control mice as of plg$^{-/-}$ mice. These data clearly indicate that fibrin deposition probably is not the reason for the more severe bacterial arthritis observed in Plg-/- mice.

Example 13

Plasminogen is Important During Host Defense Against S. aureus-Induced Infection During the Healing of Incisional Wounds in Plg-/- Mice Methods To induce incisional wound, first the dorsal sides of plg-/- mice were carefully shaved using a hair clipper and cleaned using 70% ethanol. Thereafter, a 15 mm long incision was induced along the midline on the dorsal side of the mouse. 15 min later, 1×10$^7$ CFU of S. aureus in 10 ul of PBS was topically applied and spreaded onto the open wounds. Furthermore, 50 ul of plasminogen was injected subcutaneously at two sites of the two sides of the wound openings, 5 mm away from the wound opening. For control plg-/- mice, only 50 ul of PBS was locally injected to the open wound inoculated with bacteria. Thereafter, 50 ul of plasminogen (10 ug/ul) or PBS were injected every 24 hours at similar fashion as performed at day 0 until day 10. At day 11, mice were killed and wound samples, around the wound borders and below tissue, were carefully dissected out and homogenized in 1 ml sterile PBS. After serial dilutions, the solutions of homogenates were spreaded on LB agar plates and incubated at 37° C. overnight. Viable bacterial colonies were then counted to evaluate the number of S. aureus bacteria in each homogenate.

Results

Figure 18:
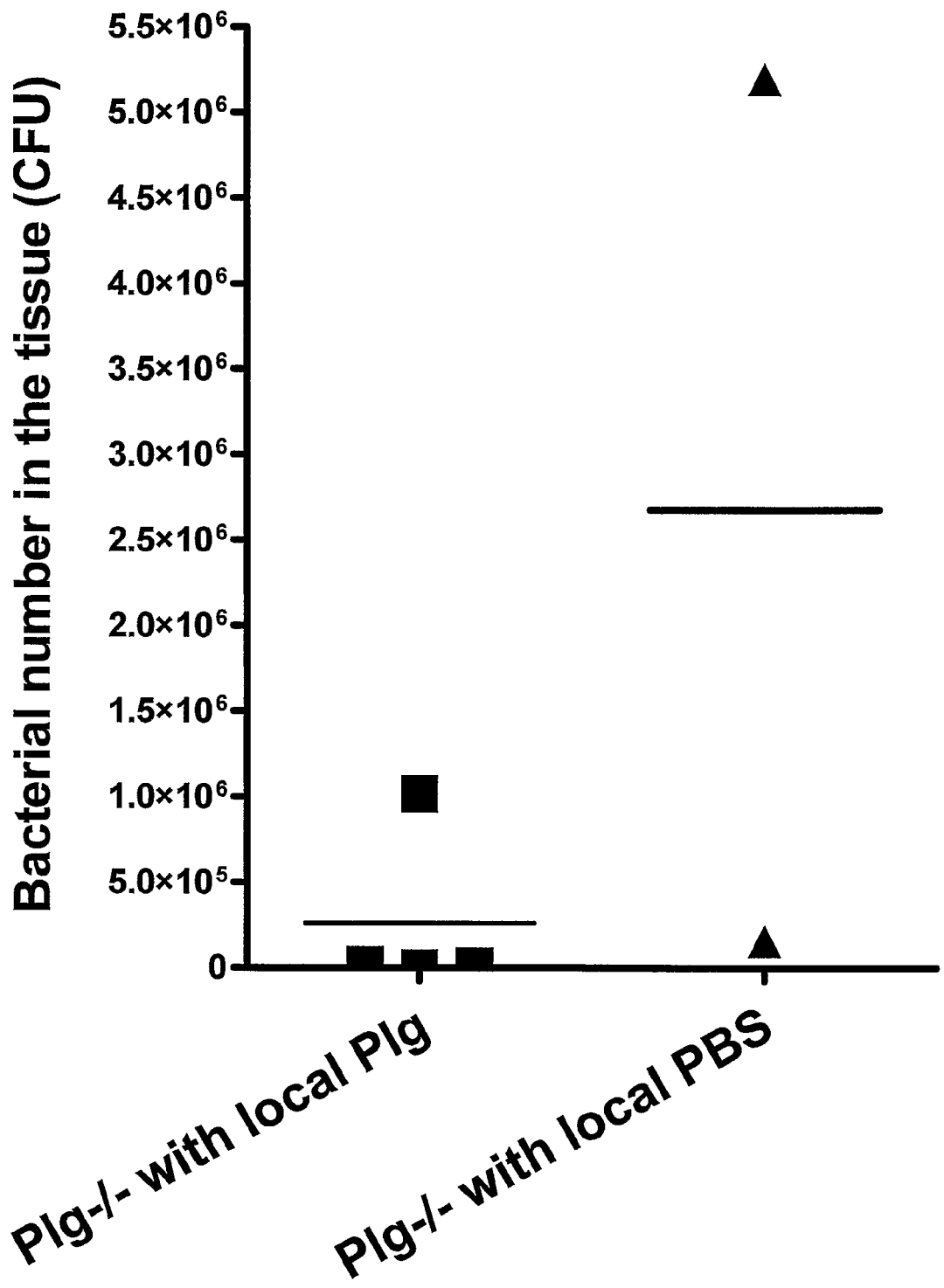
FIG. 18. Bacterial numbers in wound tissue of plg−/− mice with local treatments of plg or PBS after induction of incisional wound inoculated locally with $1 \times 10^7$ CFU of S. aureus Phillips in the dorsal skin.
Figure 19:
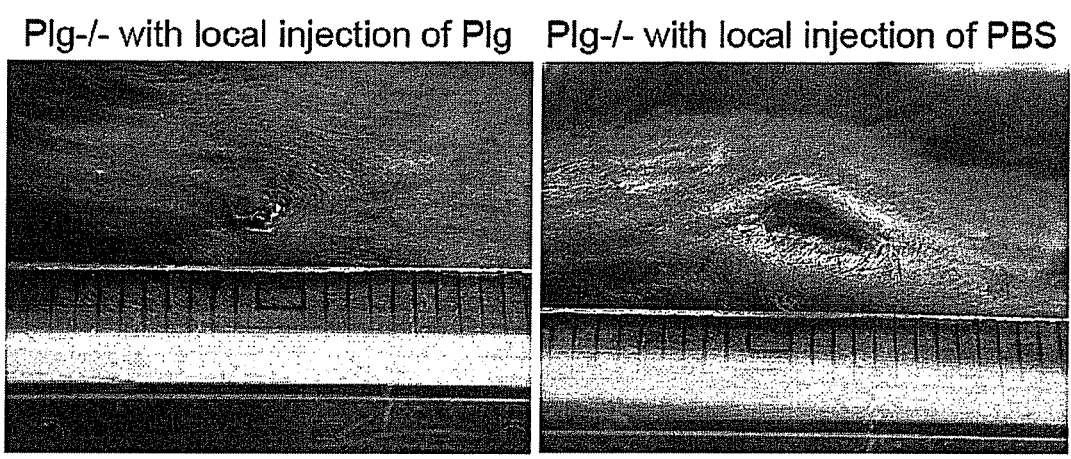
FIG. 19A-B. Representative appearance of plg−/− mice with local treatments of plg or PBS after induction of incisional wound inoculated locally with $1 \times 10^7$ CFU of S. aureus Phillips in the dorsal skin.

In order to investigate if plasminogen plays similar bacterial killing functions in an open wound infection model as in bacterial arthritis model, plg−/− mice were induced with incisional wounds and further inoculated locally with $10^7$ CFU of S. aureus Phillips. Thereafter these mice were either locally injected with human plasminogen or control PBS for 10 days. Bacterial recovery from the tissue samples of these mice show that local treatment of human plasminogen successfully lowered the number of bacteria for 10 folds as compared to the control PBS treated plg−/− mice (Table 7, FIG. 18). These data clearly show that plasminogen plays a critical role in host defense (e.g. killing of bacteria) against infections accompanied with open wound. Furthermore, local injection of plasminogen also greatly improved the healing of the infected wounds (FIG. 19). Altogether, these results indicate that plasminogen is essential in host defense against different types of traumas, as evaluated by the host defense against two types of bacterial arthritis, healing of open wounds and host defense against open wound infection.

TABLE 7

Bacterial number in plg−/− mice with local treatments of hPlg or PBS at day 11 after incisional wounding inoculated with $1 \times 10^7$ CFU of S. aureus Phillips

| Groups | Number of samples | Mean number of bacteria per gram tissue (Mean ± SE, × $10^5$ CFU/g) |
|---|---|---|
| Plg−/− with local injection of hPlg | 4 | 2.6 ± 2.5* |
| Plg−/− with local injection of PBS | 2 | 26.8 ± 25.2 |

*$P < 0.05$, compared to the group of plg−/− mice with local injection of PBS.

Example 14

Plasminogen is Important in Host Defense Against S. aureus-Induced Infection During the Healing of Burn Wounds in plg−/− Mice Methods To induce the scald burn model, mice are first put asleep by anesthesia. Thereafter the to-be-burned area is carefully shaved and placed vertically and freely by a 25 g 100 degree hot metal bar with the help of forceps for 6 seconds. The metal bar is pre-heated in hot water at boiling temperature. Six seconds of burn induces severe thermal injury to the area. Once the area is scald burned, the surface of mouse back is carefully wiped off to get rid of excessive water. Around 15 min later, 30 ul of $1 \times 10^6$ CFU of S. aureus is injected just subcutaneously at the center of the burned area. Another 15 min later, 50 ul of plasminogen (10 ug/ul) is injected subcutaneously into two sites around the edge of the scald burned area, 25 ul per site. For control plg−/− PBS group, 50 ul of PBS was injected in the same fashion as plasminogen. Thereafter from day 0 to day 9, daily injection is performed either above-below or left-right at the burned area, with the switch every day. For plg+/+ group, mice are only burned but left without any local treatment. At the end of the experiment, the wound appearance of the burns are documented by camera and tissue samples (the burned area and beneath shallow layer of tissue) are carefully dissected out and homogenized in 1 ml sterile PBS. After serial dilutions, the solutions of homogenates were spreaded on LB agar plates and incubated at 37° C. overnight. Viable bacterial colonies were then counted to evaluate the number of S. aureus bacteria in each homogenate.

Results

Figure 20:
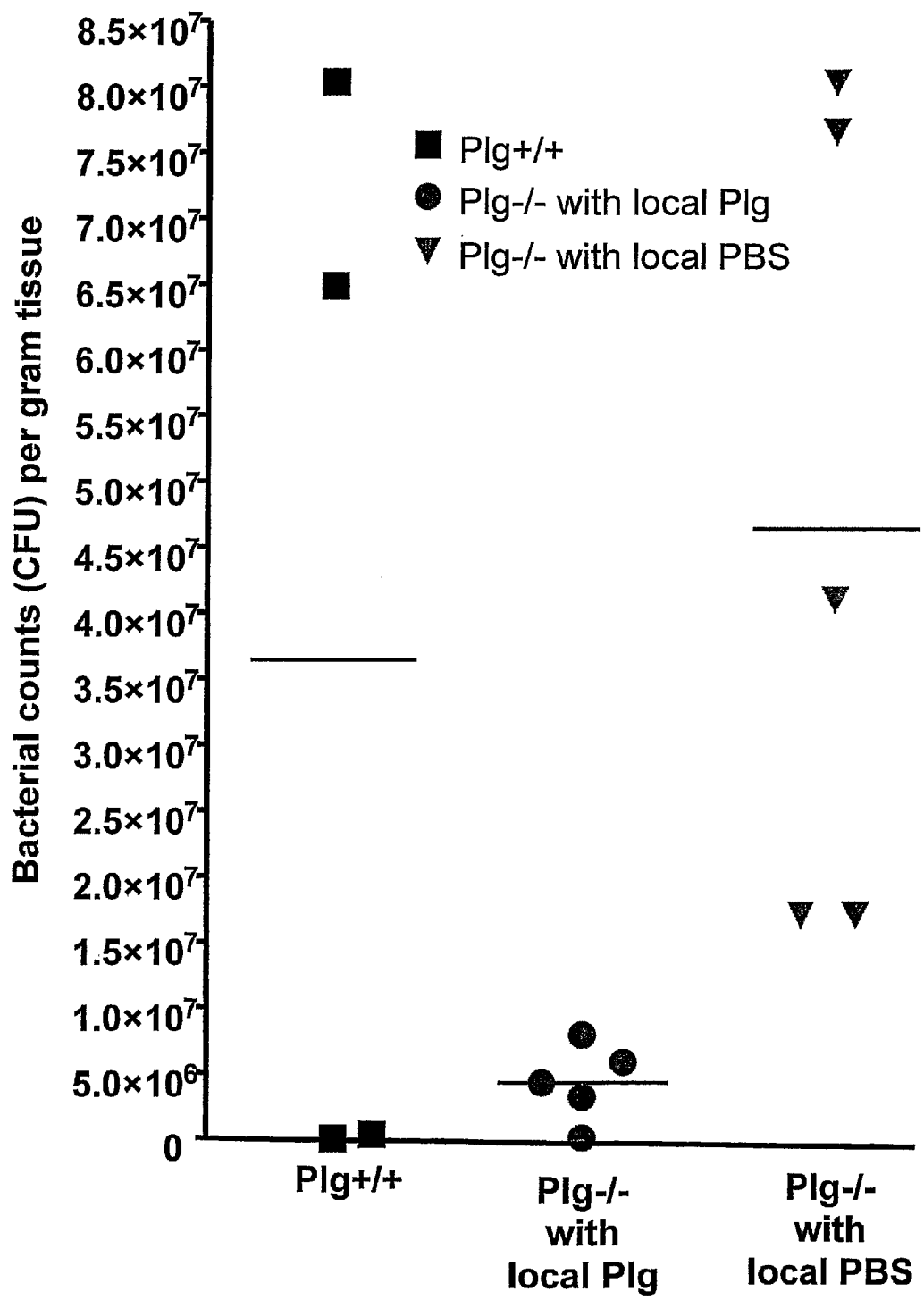
FIG. 20. Bacterial numbers in wound tissue of plg−/− mice with local treatments of plg or PBS after induction of burn wound inoculated locally with $1 \times 10^6$ CFU of S. aureus Phillips at the scald skin.

In order to investigate if plasminogen plays similar bacterial killing functions in a burn wound infection model as in bacterial arthritis model, plg−/− mice were induced with burn wounds and further inoculated locally with $1 \times 10^6$ CFU of S. aureus Phillips. Thereafter these mice were either locally injected with human plasminogen or control PBS for 9 days. Bacterial recovery from the tissue samples of these mice taken at day 10 after burn show that local treatment of human plasminogen successfully lowered the number of bacteria for 10 folds in the plg−/− mice as compared to the control PBS treated plg−/− mice (Table 8, FIG. 20), which is even lower than the bacterial number in plg+/+ mice without local injection. These data clearly show that plasminogen plays a critical role in host defense (e.g. killing of bacteria) against infections accompanied with open burn wound. Altogether, these results indicate that plasminogen is essential in host defense against different types of traumas, as evaluated by the host defense against two types of bacterial arthritis, healing of open wounds (burn, incision) and host defense against open wound infection.

TABLE 8

Bacterial number in plg−/− mice with local treatments of hPlg or PBS at day 10 after burn wounds inoculated with $1 \times 10^7$ CFU of S. aureus Phillips

| Groups | Number of samples | Mean number of bacteria per gram tissue (Mean ± SE, × $10^6$ CFU/g) |
|---|---|---|
| Plg−/− with local injection of hPlg | 5 | 0.43 ± 0.13* |
| Plg−/− with local injection of PBS | 5 | 4.6 ± 1.4 |
| Plg+/+ without local injection | 4 | 3.6 ± 2.1 |

*$P < 0.05$, compared to the group of plg−/− mice with local injection of PBS.

Example 15

Incidence of Spontaneous Chronic Otitis Media in Wild-Type and Plg-Deficient Mice Methods Experimental procedure. During an 18-week period, the mice were anaesthetized at different time intervals by an intraperitoneal injection of a 100 μl mixture of 25 μl Dormicum® (Roche A B, Stockholm, Sweden), 25 μl Hypnorm™ (Janssen Pharmaceutica, Beerse, Belgium) and 50 sterile water. The gross appearance of the tympanic membrane (TM) [SPELL OUT] was carefully examined and documented under an otomicroscope. At the end of the 18-week period, all animals were killed and from 18 animals (wild-type, n=7; plg-deficient, n=11) ears were randomly divided into three groups, aimed for bacteriological identification (wild-type, n=6; plg-deficient, n=6), plastic embedding (wild-type, n=4; plg-deficient, n=6) and paraffin embedding (wild-type, n=4; plg-deficient, n=10), respectively.

Plastic and paraffin embeddings. The skulls were collected for plastic and paraffin embedding as described previously (15). For morphology plastic-embedded samples were cross-sectioned (1 μm) through the entire MEC and stained with toluidine blue. The paraffin-embedded samples were cross-sectioned (5 μm) through the entire MEC for immunohistochemistry.
Results To study the development of chronic otitis media, 6-week old wild-type and plg-deficient mice were selected. The status of the TMs and MECs in the experimental mice was examined at the start of the experiment and at the ages of 9 weeks, 13 weeks, 18 weeks and 24 weeks. Otomicroscopically, spontaneous chronic otitis media was defined as an opaque, whitish and thickened TM, with or without effusion material in the MEC. As shown in Table 9, none of the wild-type mice (both males and females) developed any middle ear effusions or drainage from the external ear canal (EEC) during the 18-week experimental period. As revealed by otomicroscope, their TMs were thin, transparent and normally positioned (data not shown). In contrast, in the plg-deficient mice the number of ears with spontaneous otitis media gradually increased during the experimental period to a similar extent in both males and females. At the end of the experiment, spontaneous otitis media with various degrees of inflammatory changes had developed in all the ears of the remaining plg-deficient mice (Table 9).

TABLE 9

Incidence of spontaneous development of chronic otitis media in wild-type and plg-deficient mice at different ages

| Mouse group | Incidence of spontaneous development of chronic otitis media[a] at ages of: | | | | |
|---|---|---|---|---|---|
| | 6 weeks | 9 weeks | 13 weeks | 18 weeks | 24 weeks |
| Wild-type, male | 0/18 | 0/18 | 0/16 | 0/16 | 0/16 |
| Wild-type, female | 0/18 | 0/18 | 0/18 | 0/18 | 0/18 |
| Plg-deficient, male | 0/20 | 3/20 | 5/18 | 8/18 | 6/10[b] |
| Plg-deficient, female | 0/24 | 1/24 | 3/24 | 8/22 | 11/16[b] |

[a]Data are shown as the number of infected/inflamed ears divided by the total number of ears in each group.
[b]When analyzed morphologically, the middle ears in plg-deficient mice that were shown normal under otomicroscope were found to have inflammatory changes but not so pronounced, with only a thin layer of an amorphous tissue mass in the MEC adhering to the TM.

Example 16

Identification of Bacteria Isolated from the MECs of Wild-Type and Plg-Deficient Mice Methods This experiment was performed in a similar manner as Example 8, except for the bacteriological identification.

Bacteriological identification. The tympanic bullas from wild-type and plg-deficient groups were dissected free from soft tissue and a small piece of the bony floor of the bulla was removed with a knife. A sterile swab was dipped into the middle ear cavity (MEC) and by use of the swab the material was further spread over Luria-broth (LB) plates and immediately incubated at 37° C. for 48 hours. The colonies obtained were identified according to Cowan & Steel (16).

Results

At the end of the experiment, tympanic bullas from 6 wild-type and 6 plg-deficient mouse ears were randomly collected for bacterial identification. As shown in Table 10, bacteria were only found in 1 out of 6 of the wild-type samples. The bacteria were identified as *Streptococcus sanguinis*. However, in 5 out of 6 MEC samples obtained from the plg-deficient mice bacteria were isolated. The species identified were *Staphylococcus aureus*, *Micrococcus luteus*, *Streptococcus sobrinus* and *Streptococcus mutans*. All of the identified bacteria were Gram-positive.

TABLE 10

Recovery of bacteria from the MECs in wild-type and plg-deficient mice at the age of 24 weeks.

| Mouse ear number | Bacterial findings in | |
|---|---|---|
| | Wild-type | Plg-deficient |
| 1 | *Streptococcus sanguinis* | *Staphylococcus aureus* |
| 2 | ND[a] | *Micrococcus luteus* |
| 3 | ND | *Streptococcus sobrinus* |
| 4 | ND | *Streptococcus sobrinus* and *Streptococcus mutans* |
| 5 | ND | *Streptococcus mutans* |
| 6 | ND | ND |

[a]ND, not detectable.

Example 17

Light Microscopical Studies of the Middle Ears in Wild-Type and Plg-Deficient Mice Methods This experiment was performed in a similar manner as Example 8, except for the immunohistochemical stainings.

Immunohistochemical stainings. The paraffin-embedded sections were re-hydrated in a series of decreasing ethanol concentrations and rinsed in distilled water. Endogenous peroxidase activity was blocked with 3% $H_2O_2$ for 10 min and the slides were further washed in PBS. The consecutive sections were then treated with antibodies indicated below. In all immunohistochemical stainings, adjacent slides incubated with sera from non-immunized animals instead of the primary antibody were used as negative controls.

For detection of inflammatory cells, rat anti-mouse monoclonal primary antibodies against T cells (Clone 53-7.3, dilution 1:50; BD Biosciences Pharmingen, Stockholm, Sweden), B cells (Clone RA3-6B2, dilution 1:250; BD Biosciences Pharmingen), macrophages (MCAP497, dilution 1:500; Serotec, Oxford, U.K.) and neutrophils (CL8993AP, dilution 1:200; Cedarlane Laboratories, Hornby, Ontario, Canada) were used. To perform immunohistochemical stainings, slides were first retrieved and incubated with normal rabbit serum (Dako Patts, Copenhagen, Denmark) before incubated with different primary antibodies at the appropriate concentrations. Thereafter the slides were incubated with biotinylated rabbit anti-rat IgG (Dako Patts) and further treated using the avidin-biotin-peroxidase complex (ABC) method (Vector Laboratories, Burlingame, Calif.).

Cytokeratin was detected immunohistochemically by the peroxidase anti-peroxidase (PAP) method using a rabbit anti-human polyclonal antibody (10550, ICN Pharmaceuticals, Aurora, Ohio) as the primary antibody. In brief, the slides containing tissue sections were first retrieved with 0.1% trypsin (pH 7.8) at 37° C. for 8 min, blocked with 5% non-immunized swine serum (Dako Patts), and incubated with the primary antibody diluted 1:100 in PBS. After this a swine anti-rabbit link antibody (Dako Patts) was applied, followed by a rabbit PAP complex (Dako Patts).

Fibrin(ogen) was detected immunohistochemically by the PAP method using a goat anti-mouse polyclonal antibody (Nordic Immunological Laboratories, Tilburg, The Netherlands) as the primary antibody. After initial incubation with rabbit serum (Dako Patts) and then with the primary antibody at a dilution of 1:500 in PBS, the slides were incubated with a rabbit anti-goat link antibody (Dako Patts). Thereafter, the slides were incubated with goat PAP complex (Dako Patts).

All the slides were visualized as the brown precipitates by a diaminobenzidine (DAB) reaction (Vector Laboratories) and counter-stained with Mayer's hematoxylin. The slides were examined by light microscope under a Leica DMLB microscope and images were recorded digitally using a Leica DC 300F camera connected to a personal computer. Adjustment of contrast and brightness in individual images were performed using the Adobe Photoshop 7.0 software.

Results

Figure 7:
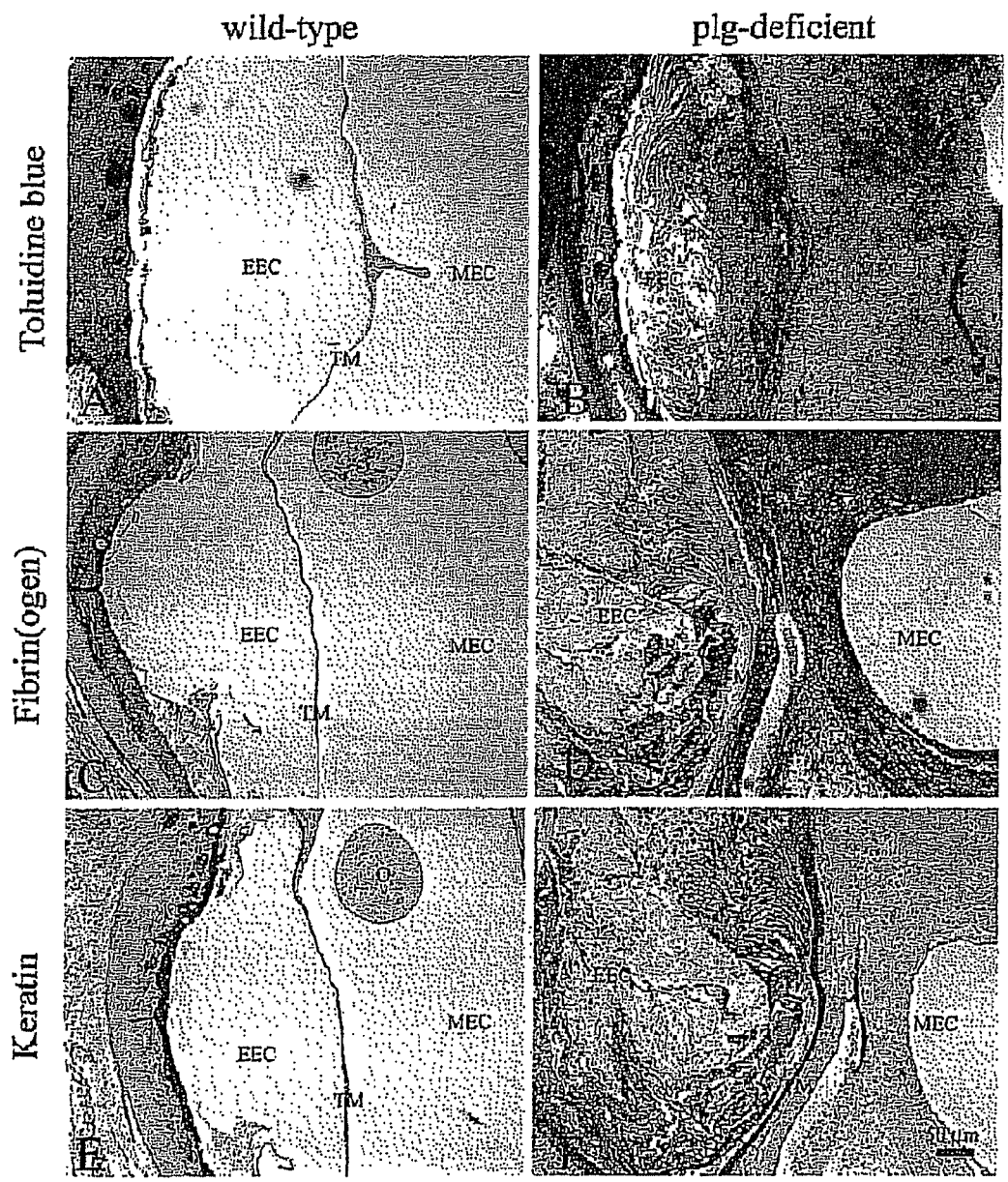
FIG. 7A-F. Morphology of representative middle ear sections from wild-type mice and plg-deficient mice, stained with toluidine blue (A and B) and immunohistochemical stainings for fibrin (C and D) and keratin (E and F). A. The middle ear from a wild-type mouse. No effusion material is detected in the middle ear cavity (MEC). B. The middle ear from a plg-deficient mouse. Otitis media is present in the MEC. C and D. The middle ears from a wild-type mouse and plg-deficient mouse respectively, analyzed by immunohistochemical staining for fibrin(ogen). E and F. The middle ears from a wild-type mouse and plg-deficient mouse respectively, analyzed with immunohistochemical staining for keratin. O, ossicle. Bar 50 µm.

At the end of the experiment, morphological staining was performed on plastic-embedded samples from wild-type and plg-deficient mice. As shown in FIG. 7A, the TMs and the middle ears of wild-type mice exhibited a normal structure. The TM revealed a typical thin three-layered structure: an outer keratinized epidermal layer, a middle lamina propria and an inner epithelial lining contiguous with that of the MEC. There were no middle ear effusions detected in the MEC. However, in the plg-deficient mice, inflammatory changes were observed in all the middle ears examined. The TM was thickened and adhered with an amorphous tissue mass which sometimes filled up almost the entire MEC (FIG. 7B). In many of the samples the EEC was also filled with an amorphous tissue (FIG. 7D).

At the end of the experimental period, immunohistochemical stainings were performed to study the distribution of fibrin and keratin in the middle ear (FIGS. 7C, 7D, 7E, 7F). In wild-type mice, only weak immunoreactivity against fibrin (ogen) and keratin was observed at the epithelial surface of the TM (FIGS. 7C and 7E). However, in the plg-deficient mice, as shown in FIG. 7D, an amorphous tissue covering the mucosa of the TM and MEC was observed to have immunoreactivity against fibrin. The structure of the amorphous tissue varied in different areas and in different samples, from loose-net-like to smear-like, or even densely packed (data not shown). Fibrin immunoreactivity was also observed in the amorphous tissue in the EEC. In most of the plg-deficient mice, the keratin staining layer in the TM and surrounding epidermal layer of the EEC was considerably thickened (FIG. 7F).

Figure 8:
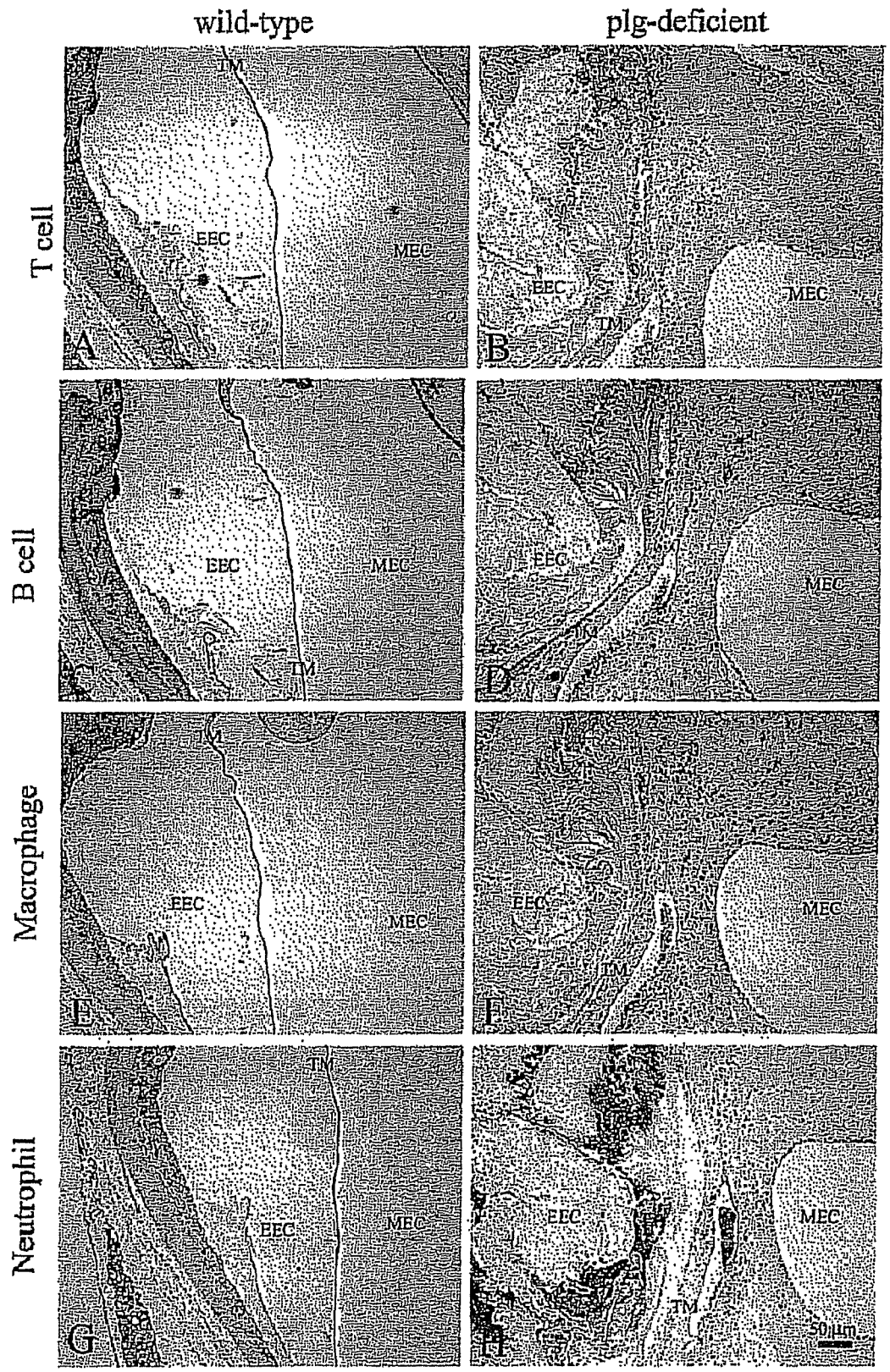
FIG. 8A-H. Immunohistochemical stainings for T cells, B cells, macrophages and neutrophils in middle ears of wild-type and plg-deficient mice. Middle ears from a wild-type control (A, C, E, G) and a representative plg-deficient mouse (B, D, F, H) were analyzed by immunohistochemical stainings of T cells (A and B), B cells (C and D), macrophages (E and F) and neutrophils (G and H). O, ossicle. Bar 50 µm.

To study the infiltration of inflammatory cells, paraffin sections from wild-type and plg-deficient mice were stained for T cells, B cells, macrophages and neutrophils. As shown in FIGS. 8A, 8C, 8E and 8G, hardly any inflammatory cells were detectable in the TM and in the middle ear mucosa of the wild-type mice. In plg-deficient mice, however, T cells, B cells, macrophages and neutrophils were all found in the TM and the amorphous tissue filling the middle ear and EEC (FIGS. 8B, 2D, 8F and 8H). T cells and B cells were relatively fewer and they were sparsely distributed in the TM and the middle ear mucosa (FIGS. 8B and 8D). In the middle ear mucosa macrophages were the most abundant inflammatory cell type (FIG. 8F) and neutrophils were the dominating cell type in the amorphous tissue extending into the EEC (FIG. 8H). Overall, these results suggest that plasminogen plays an essential role in protecting against the spontaneous development of chronic otitis media.

The foregoing Examples are presented by way of illustration and are not intended to in any way limit the scope of the present invention as set out in the appended claims. All references set out in the description are incorporated by reference.

REFERENCE LIST

1. Aderem, A. 2003. Phagocytosis and the inflammatory response. *J. Infect. Dis.* 187 Suppl 2:S340-S345.
2. Hauschildt, S., and Kleine, B. 1995. Bacterial stimulators of macrophages. *Int. Rev. Cytol.* 161:263-331.
3. Chertov, O., Yang, D., Howard, O. M., and Oppenheim, J. J. 2000. Leukocyte granule proteins mobilize innate host defenses and adaptive immune responses. *Immunol. Rev.* 177:68-78.
4. Ny, A., Leonardsson, G., Hagglund, A. C., Hagglof, P., Ploplis, V. A., Carmeliet, P., and Ny, T. 1999. Ovulation in plasminogen-deficient mice. *Endocrinology* 140:5030-5035.
5. Teele, D. W., Klein, J. O., and Rosner, B. 1989. Epidemiology of otitis media during the first seven years of life in children in greater Boston: a prospective, cohort study. *J. Infect. Dis.* 160:83-94.
6. Alexander C M, and Werb, Z. 1991. Extracellular matrix degradation. In *Cell Biology of Extracellular Matrix*. Hay E D, editor. Plenum Press. New York. 255-302.
7. Travis, J., and Salvesen, G. 1983. Control of coagulation and fibrinolysis by plasma proteinase inhibitors. *Behring Inst. Mitt.* 56-65.
8. Wiman, B., and Wallen, P. 1975. Structural relationship between "glutamic acid" and "lysine" forms of human plasminogen and their interaction with the NH2-terminal activation peptide as studied by affinity chromatography. *Eur. J. Biochem.* 50:489-494.
9. Saksela, O., and Rifkin, D. B. 1988. Cell-associated plasminogen activation: regulation and physiological functions. *Annu. Rev. Cell Biol.* 4:93-126.
10. Collen, D., and Lijnen, H. R. 1991. Basic and clinical aspects of fibrinolysis and thrombolysis. *Blood* 78:3114-3124.
11. Liu, Z. Q., Deng, G. M., Foster, S., and Tarkowski, A. 2001. Staphylococcal peptidoglycans induce arthritis. *Arthritis Res.* 3:375-380.
12. Qasimi, P., Ming-Lum, A., Ghanipour, A., Ong, C. J., Cox, M. E., Ihle, J., Cacalano, N., Yoshimura, A., and Mui, A. L. 2006. Divergent mechanisms utilized by SOCS3 to mediate interleukin-10 inhibition of tumor necrosis factor alpha and nitric oxide production by macrophages. *J. Biol. Chem.* 281:6316-6324.
13. Gjertsson, I., Hultgren, O. H., and Tarkowski, A. 2002. Interleukin-10 ameliorates the outcome of *Staphylococcus aureus* arthritis by promoting bacterial clearance. *Clin. Exp. Immunol.* 130:409-414.
14. Carmeliet, P., Schoonjans, L., Kieckens, L., Ream, B., Degen, J., Bronson, R., De, V. R., van den Oord, J. J., Collen, D., and Mulligan, R. C. 1994. Physiological consequences of loss of plasminogen activator gene function in mice. *Nature* 368:419-424.
15. Eriksson, P. O., Mattsson, C., and Hellstrom, S. 2003. First forty-eight hours of developing otitis media: an experimental study. *Ann. Otol. Rhinol. Laryngol.* 112:558-566.
16. COWAN, S. T., and STEEL, K. J. 1961. Diagnostic tables for the common medical bacteria. *J. Hyg.* (Lond) 59:357-372.

The invention claimed is:

1. A method for the prophylaxis or treatment of joint infection or bacterial arthritis caused by *Staphylococcus aureus*, which comprises administering a pharmaceutical composition comprising an effective amount of plasminogen to a subject in need thereof.

2. The method of claim 1, wherein the disease is bacterial arthritis.

3. The method of claim 1, wherein the disease is joint infection.

4. The method of claim 1, wherein the pharmaceutical composition further comprises at least one antibiotic agent.

5. The method of claim 4, wherein the antibiotic agent is selected from the group consisting of tetracyclines, amphenicols, beta-lactams, penicillins, sulphonamides, macrolides, lincosamides, streptogamins, streptomycins, quinolones and metronidazoles.

6. The method of claim 1, wherein the subject is a mammal.

7. The method of claim 1, wherein the subject is deficient in plasmin or plasminogen.

8. The method of claim 7, wherein the deficiency is selected from the group consisting of congenital, acquired, and local.

9. The method of claim 1, wherein the pharmaceutical composition is administered by a method selected from the group consisting of systemically, locally, topically, intravenously, intramuscularly, subcutaneously, via inhalation, intrathecally, via local injection, via intra-articular injection, and per rectally.

10. The method of claim 1, wherein the pharmaceutical composition is administered in combination with a suitable polypeptide carrier or stabilizing agent.

11. The method of claim 1, wherein the pharmaceutical composition is administered at a dose of 0.05 mg to about 10 mg.

12. The method of claim 1, wherein the administration of the pharmaceutical composition is repeated at least once.

13. The method of claim 1, wherein administering a pharmaceutical composition is performed by applying a wound dressing, comprising the pharmaceutical composition, to an infected area.

14. The method of claim 1, wherein the method further comprises inducing an immune response against an infectious pathogen.

15. The method of claim 6, wherein the mammal is a human.

16. The method of claim 11, wherein the pharmaceutical composition is administered at a dose from about 0.5 to about 5 mg.

17. The method of claim 12, wherein the administration of the pharmaceutical composition is repeated at least every day.

* * * * *